United States Patent
Wrasidlo

(10) Patent No.: US 9,284,309 B2
(45) Date of Patent: Mar. 15, 2016

(54) DI- AND TRI-HETEROARYL DERIVATIVES AS INHIBITORS OF PROTEIN AGGREGATION

(71) Applicant: Neuropore Therapies, Inc., San Diego, CA (US)

(72) Inventor: Wolfgang Wrasidlo, San Diego, CA (US)

(73) Assignee: NEUROPORE THERAPIES, INC., San Diego, CA (US)

( * ) Notice: Subject to any disclaimer, the term of this patent is extended or adjusted under 35 U.S.C. 154(b) by 0 days.

(21) Appl. No.: 14/415,120

(22) PCT Filed: Jul. 16, 2013

(86) PCT No.: PCT/US2013/050719
§ 371 (c)(1),
(2) Date: Jan. 15, 2015

(87) PCT Pub. No.: WO2014/014937
PCT Pub. Date: Jan. 23, 2014

(65) Prior Publication Data
US 2015/0183776 A1    Jul. 2, 2015

Related U.S. Application Data

(60) Provisional application No. 61/672,239, filed on Jul. 16, 2012.

(51) Int. Cl.
*A61K 31/496*   (2006.01)
*C07D 417/12*   (2006.01)
*C07D 417/14*   (2006.01)

(52) U.S. Cl.
CPC ............ *C07D 417/14* (2013.01); *C07D 417/12* (2013.01)

(58) Field of Classification Search
None
See application file for complete search history.

(56) References Cited

U.S. PATENT DOCUMENTS

| | | |
|---|---|---|
| 6,784,195 B2 | 8/2004 | Hale et al. |
| 7,138,420 B2 | 11/2006 | Bentzien et al. |
| 8,846,682 B2 * | 9/2014 | Masliah et al. .......... 514/252.16 |
| 2003/0195241 A1 | 10/2003 | Hale et al. |
| 2010/0280045 A1 | 11/2010 | Hamblin et al. |
| 2011/0288083 A1 | 11/2011 | Cardozo et al. |
| 2012/0083475 A1 | 4/2012 | Griffioen et al. |

FOREIGN PATENT DOCUMENTS

WO    WO -2011/084642    7/2011

OTHER PUBLICATIONS

Blazer et al. Neuropsychopharmacology Reviews (2009) 34, 126-141.*
Tutar et al. Role of Protein Aggregation in Neurodegenerative Disease, pp. 1-22 (2013) obtained from the Internet at http://dx.doi.org/10.5772/54487 on Jul. 13, 2015.*
Bagshawe, "Antibody-Directed Enzyme Prodrug Therapy: A Review," Drug Dev. Res. (1995) 34:220-230.
Bartlett et al., "Transaminations of NN-Dimethylformamide Azine," J. Chem. Soc. (C) (1967)1664-1666.
Berge et al., "Pharmaceutical Salts," J. Pharm. Sci. (1977) 66(1):1-19.
Bertolini et al., "A New Rational Hypothesis for the Pharmacophore of the Active Metabolite of Leflunomide, a Potent Immunosuppressive Drug," J. Med. Chem. (1997) 40(13):2011-2016.
Bodor, "Novel Approaches to the Design of Safer Drugs: Soft Drugs and Site-Specific Chemical Delivery Systems," Adv. Drug Res. (1984) 13:255-331.
Clapp, 1,2,4-Oxadiazoles,: in Advances in Heterocyclic Chemistry (1976) vol. 20, p. 65.
Finnegan et al., "An Improved Synthesis of 5-Substituted Tetrazoles," J. Am. Chem. Soc. (1958) 80:3908-3911.
Fleming et al., "Early and Progressive Sensorimotor Anomalies in Mice Overexpressing Wild-Type Human α-Synuclein," J. Neurosci. (2004) 24(42):9434-9440.
Goddard, "5-Heteroaryl-2-Thiophenecarboxylic Acids: Oxazoles and Oxadiazoles," J. Het. Chem. (1991) 28:17-28.
Hashimoto et al., "β-Synuclein Inhibits α-Synuclein Aggregation: A Possible Role as an Anti-Parkinsonian Factor," Neuron (2001) 32:213-223.
International Search Report and Written Opinion for PCT/US13/50719, mailed Dec. 19, 2013, 8 pages.
Loudon, Organic Chemistry, Fourth Edition, New York: Oxford University Press (2002) pp. 360-361, 1084-1085.
Masliah et al., "Dopaminergic Loss and Inclusion Body Formation in α-Synuclein Mice: Implications for Neurodegenerative Disorders," Science (2000) 287(5456):1265-1269.
Rockenstein et al., "Differential Neuropathological Alterations in Transgenic Mice Expressing α-Synuclein from the Platelet-derived Growth Factor and Thy-1 Promoters," J. Neurosci. Res. (2002) 68(5):568-578.
Shan et al., "Prodrug Strategies Based on Intramolecular Cyclization Reactions," J. Pharm. Sci. (1997) 86(7):765-767.
Streitwieser et al., Introduction to Organic Chemistry, 3rd ed. (1985) Chapter 31, pp. 998-1047.
Wadsworth et al., "Synthesis and Muscarinic Activities of Quinuclidin-3-yltriazole and -tetrazole derivatives," J. Med. Chem. (1992) 35:1280-1290.

* cited by examiner

*Primary Examiner* — Emily Bernhardt
(74) *Attorney, Agent, or Firm* — Morrison & Foerster LLP

(57) ABSTRACT

The present invention relates to certain di- and tri-heteroaryl derivatives, pharmaceutical compositions containing them, and methods of using them, including methods for preventing, reversing, slowing, or inhibiting protein aggregation, and methods of treating diseases that are associated with protein aggregation, including neurodegenerative diseases such as Parkinson's disease, Alzheimer's disease, Lewy body disease, and multiple system atrophy.

20 Claims, No Drawings

DI- AND TRI-HETEROARYL DERIVATIVES AS INHIBITORS OF PROTEIN AGGREGATION

CROSS-REFERENCE TO RELATED APPLICATIONS

This application is a U.S. National Stage of International Application No. PCT/US2013/050719 filed on Jul. 16, 2013, which claims priority to U.S. Provisional Application No. 61/672,239, filed Jul. 16, 2012. The contents of these applications are incorporated herein by reference in their entirety.

TECHNICAL FIELD

The present invention relates to certain di- and tri-heteroaryl derivatives, pharmaceutical compositions containing them, and methods of using them, including methods for preventing, reversing, slowing, or inhibiting protein aggregation, and methods of treating diseases that are associated with protein aggregation, including neurodegenerative diseases such as Parkinson's disease, Alzheimer's disease, Lewy body disease, and multiple system atrophy.

BACKGROUND ART

Neurodegenerative disorders of the aging population such as Alzheimer's disease (AD), Parkinson's disease (PD), and fronto-temporal dementia (FTD), affect over 20 million people in the United States and European Union alone and rank among the top causes of death for the elderly. A common feature among these neurological disorders is the chronic accumulation of proteins into neurotoxic aggregates. Each disease is characterized by the specific neuronal populations that are affected, the particular protein aggregates that are involved, and the clinical features that result from the neuronal degeneration.

Studies suggest that the initial stages of protein aggregation involve mutation or post-translational modification (e.g., nitrosilation, oxidation) of the target protein, which then adopts an abnormal conformation that facilitates interactions with similarly misfolded proteins. The abnormal proteins then aggregate to form dimers, trimers, and higher-order multimers, also termed "soluble oligomers," which may disrupt synaptic function. Additionally, the aggregates may then anchor in the cell membrane and form globular oligomers (which in turn can form pores in the membrane) and/or protofibrils or fibrils. These larger, insoluble fibrils may function as reservoirs of the bioactive oligomers.

The particular proteins implicated in these neurodegenerative diseases vary in identity and source. For example, in AD, the neurotoxic aggregates are composed of the secreted protein amyloid-beta (Aβ). In idiopathic Parkinson's disease (IPD), dementia with Lewy bodies (LBD), PD dementia (PDD), and multiple system atrophy (MSA), the neurotoxic aggregates are composed of α-synuclein (SYN), which is a synaptic protein that is intracellular under normal conditions. In FTD and amyotrophic lateral sclerosis (ALS), neurotoxic aggregates originate from other intracellular proteins such as tau, TDP-43, or SOD1. For certain diseases, such as AD, SYN aggregates with the primary protein. Thus, compounds that interferer with SYN aggregation may impact neurodegenerative pathologies of various etiologies.

Two mechanisms are implicated in these neurodegenerative processes. In the first, the misfolded and/or aggregated proteins anchor to the various cell membrane structures. Binding of the misfolded or aggregated molecules to the plasma membrane or the membranes of organelles (e.g., mitochondria or lysosomes) may interfere with protein transcription, autophagy, mitochondrial function, and pore formation. By way of example, neurotoxic SYN aggregates and interacts with lipids in cell membranes, by a specific portion of the c-terminal region of the synuclein protein. Compounds that bind to this region can inhibit protein-protein or protein-lipid interactions and can therefore be used to block neurotoxic SYN oligomerization and membrane interaction. In the second process, aggregated protein is released from the anchored subunit and propagates to adjacent cells. This cell-to-cell propagation of toxic protein aggregates may then underlie the anatomic progression of neurodegeneration and worsening of symptoms. Small molecule drugs that interact with the target proteins may limit release and/or propagation, and therefore reduce the neurotoxic effects of aggregated proteins. Such compounds may therefore provide new therapies for AD, PD, LBD, MSA, and related neurodegenerative conditions.

There remains a need for inhibitors of protein aggregation with desirable pharmaceutical properties. Certain di- and tri-heteroaryl derivatives have been found in the context of this invention to have protein aggregation modulating activity.

SUMMARY OF THE INVENTION

In one aspect, the invention relates to a chemical entity of the following Formula (I):

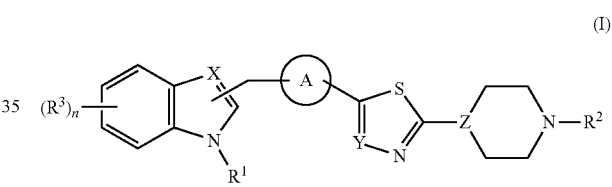

(I)

wherein

X, Y, and Z are each independently CH or N;

$R^1$ is H, $C_{1-6}$alkyl, or $C_{3-7}$cycloalkyl;

$R^2$ is H, $C_{1-6}$alkyl, or $C_{3-7}$cycloalkyl;

each $R^3$ is independently halogen, hydroxy, $C_{1-4}$alkoxy, cyano, amino, or —$CF_3$;

n is 0, 1, or 2; and

A moiety is:

(a) a 5-membered heteroaryl ring substituted with $C_{1-6}$alkyl; or

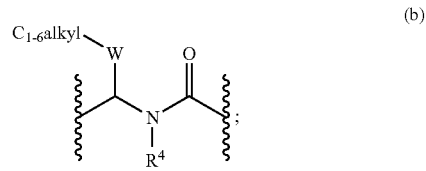

(b)

wherein W is a 5-membered heteroaryl ring, —C(O)NHNHC(O)—, —C(NH)NH—, or —C(O)NHNH—; and $R^4$ is H or $C_{1-6}$alkyl;

or a pharmaceutically acceptable salt thereof.

In another aspect, the invention relates to a chemical entity of the following Formula (II):

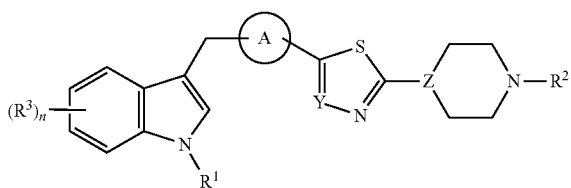

(II)

wherein
Y is CH or N;
$R^1$ is H, $C_{1-6}$alkyl, or $C_{3-7}$cycloalkyl;
$R^2$ is H, $C_{1-6}$alkyl, or $C_{3-7}$cycloalkyl;
each $R^3$ is independently halogen, hydroxy, $C_{1-4}$alkoxy, cyano, amino, or —$CF_3$;
n is 0, 1, or 2; and
A moiety is:
 (a) a 5-membered heteroaryl ring substituted with $C_{1-6}$alkyl; or

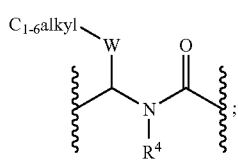

(b)

wherein W is a 5-membered heteroaryl ring, —C(O)NHNHC(O)—, —C(NH)NH—, or —C(O)NHNH—; and
$R^4$ is H or $C_{1-6}$alkyl;
or a pharmaceutically acceptable salt thereof.

In another aspect, the invention relates to a chemical entity of the following Formula (III):

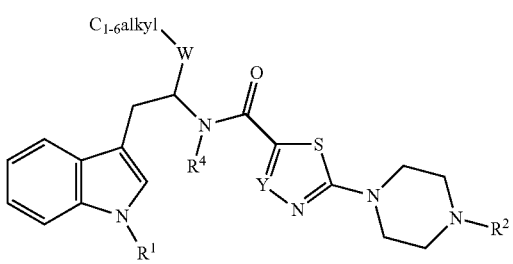

(III)

wherein
Y is CH or N;
$R^1$ is H or $C_{1-6}$alkyl;
$R^2$ is H or $C_{1-6}$alkyl;
$R^4$ is H or $C_{1-6}$alkyl; and
W is a 5-membered heteroaryl ring, —C(O)NHNH—C(O)—, —C(O)NHNH—, or —C(NH)NH—;
or a pharmaceutically acceptable salt thereof.

In certain embodiments, the compound of Formula (I), (II), or (III) is a compound selected from those species described or exemplified in the detailed description below.

In a further aspect, the invention relates to a pharmaceutical composition comprising at least one compound of Formula (I), (II), or (III) or a pharmaceutically acceptable salt thereof. Pharmaceutical compositions according to the invention may further comprise a pharmaceutically acceptable excipient.

The invention is also a compound of Formula (I), (II), or (III) or a pharmaceutically acceptable salt thereof for use as a medicament.

In another aspect, the invention is directed to a method of treating a neurodegenerative disease or condition associated with protein aggregation comprising administering to a subject in need of such treatment an effective amount of at least one compound of Formula (I), (II), or (III) or a pharmaceutically acceptable salt thereof.

In another aspect, the invention is directed to a method of treating a disease or medical condition associated with protein aggregation, comprising administering to a subject in need of such treatment an effective amount of at least one compound of Formula (I), (II), or (III) or a pharmaceutically acceptable salt thereof. The invention is also directed at use of a compound of Formula (I), (II), or (III) in the preparation of a medicament for the treatment of such diseases and medical conditions, and the use of such compounds and salts for treatment of such diseases and medical conditions.

In yet another aspect, the invention relates to a method of interfering with the accumulation of protein or peptide aggregation in a cell, or preventing, slowing, reversing, or inhibiting protein or peptide aggregation in a cell, comprising contacting the cell with an effective amount of at least one compound of Formula (I), (II), or (III) or a salt thereof, and/or with at least one pharmaceutical composition of the invention, wherein the contacting is in vitro, ex vivo, or in vivo.

One of ordinary skill in the art will recognize that compounds of Formula (II) and Formula (III) are compounds of Formula (I).

Additional embodiments, features, and advantages of the invention will be apparent from the following detailed description and through practice of the invention.

For the sake of brevity, the disclosures of the publications cited in this specification, including patents, are herein incorporated by reference.

DETAILED DESCRIPTION OF THE INVENTION

The present invention relates to certain di- and tri-heteroaryl derivatives, pharmaceutical compositions containing them, and methods of using them, including methods for preventing, reversing, slowing, or inhibiting protein aggregation, and methods of treating diseases that are associated with protein aggregation, including neurodegenerative diseases such as Parkinson's disease, Alzheimer's disease, Lewy body disease, and multiple system atrophy.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about". It is understood that, whether the term "about"

is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

The nomenclature used herein to name the subject compounds is illustrated in the Examples herein. This nomenclature has generally been derived using the commercially-available AutoNom software (MDL, San Leandro, Calif.).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such sub-combination of chemical groups was individually and explicitly disclosed herein.

Representative Embodiments

Formula (I)

In one aspect, the invention relates to a chemical entity of the following Formula (I):

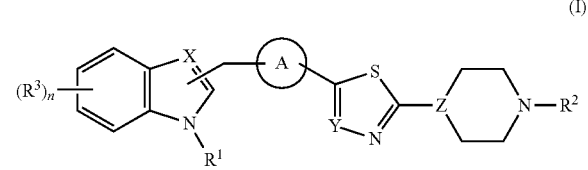

wherein
X, Y, and Z are each independently CH or N;
$R^1$ is H, $C_{1-6}$alkyl, or $C_{3-7}$cycloalkyl;
$R^2$ is H, $C_{1-6}$alkyl, or $C_{3-7}$cycloalkyl;
each $R^3$ is independently halogen, hydroxy, $C_{1-4}$alkoxy, cyano, amino, or —$CF_3$;
n is 0, 1, or 2; and
A moiety is:
(a) a 5-membered heteroaryl ring substituted with $C_{1-6}$alkyl; or

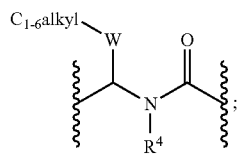

wherein W is a 5-membered heteroaryl ring, —C(O)NHNHC(O)—, —C(NH)NH—, or —C(O)NHNH—; and
$R^4$ is H or $C_{1-6}$alkyl;
or a pharmaceutically acceptable salt thereof.

In some embodiments of Formula (I), X is CH. In certain instances, X is N. In certain instances, Y is CH. In certain instances, Y is CH. In certain instances, Z is CH. In certain instances, Z is N.

In some embodiments of Formula (I), $R^1$ is H or $C_{1-6}$alkyl. In certain instances, $R^1$ is $C_{1-6}$alkyl. In certain instances, $R^1$ is methyl or ethyl. In certain instances, $R^1$ is methyl. In certain instances, $R^1$ is H or methyl. In certain instances, $R^1$ is $C_{3-7}$cycloalkyl. In certain instances, $R^1$ is cyclopropyl, cyclobutyl, cyclopentyl, or cyclohexyl.

In some embodiments of Formula (I), $R^2$ is H or $C_{1-6}$ alkyl. In certain instances, $R^2$ is methyl or ethyl. In certain instances, $R^2$ is H or methyl. In certain instances, $R^2$ is $C_{3-7}$cycloalkyl. In certain instances, $R^2$ is cyclopropyl, cyclobutyl, cyclopentyl, or cyclohexyl.

In some embodiments of Formula (I), each $R^3$ is independently Br, Cl, F, hydroxy, methoxy, cyano, amino, or —$CF_3$.

In some embodiments of Formula (I), n is 0 or 1. In other embodiments, n is 0.

In some embodiments of Formula (I), A moiety is a 5-membered heteroaryl ring substituted with $C_{1-6}$alkyl. In certain instances, the 5-membered heteroaryl ring contains one, two, three, or four heteroatoms selected from the group consisting of N, S, and O. In certain instances, the 5-membered heteroaryl ring contains one, two, or three heteroatoms. In certain instances, A moiety is pyrrolyl, pyrazolyl, imidazolyl, furanyl, oxazolyl, oxadiazolyl, thienyl, thiazolyl, thiadiazolyl, triazolyl, or tetrazolyl, each substituted with $C_{1-6}$alkyl. In certain instances, A moiety is imidazolyl or 1,3,4-triazolyl, each substituted with $C_{1-6}$alkyl.

In other embodiments, A moiety is

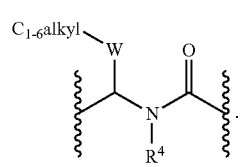

In some embodiments, W is a 5-membered heteroaryl ring. In certain instances, the 5-membered heteroaryl ring contains one, two, three, or four heteroatoms selected from the group consisting of N, S, and O. In certain instances, the 5-membered heteroaryl ring contains one, two, or three heteroatoms. In other embodiments, W is pyrrolyl, pyrazolyl, imidazolyl, furanyl, oxazolyl, oxadiazolyl, thienyl, thiazolyl, thiadiazolyl, triazolyl, or tetrazolyl. In certain instances, W is tetrazolyl, thiazolyl, thiadiazolyl, triazolyl, or oxadiazolyl, each substituted with $C_{1-6}$alkyl. In certain instances, W is tetrazolyl, thiazolyl, thiadiazolyl, triazolyl, or oxadiazolyl, and the attached $C_{1-6}$alkyl is methyl, ethyl, propyl, or butyl.

In other embodiments of Formula (I), W is —C(O)NHNHC(O)—, —C(NH)NH—, or —C(O)NHNH—.

In some embodiments of Formula (I), $R^4$ is H, methyl, ethyl, propyl, or isopropyl. In other embodiments, $R^4$ is H.

Formula II

In another aspect, the invention provides for compounds of Formula (II):

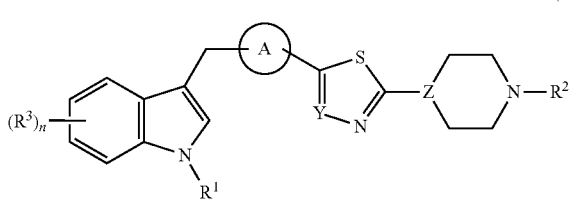

(II)

wherein
Y is CH or N;
$R^1$ is H, $C_{1-6}$alkyl, or $C_{3-7}$cycloalkyl;
$R^2$ is H, $C_{1-6}$alkyl, or $C_{3-7}$cycloalkyl;
each $R^3$ is independently halogen, hydroxy, $C_{1-4}$alkoxy, cyano, amino, or —$CF_3$;
n is 0, 1, or 2; and
A moiety is:
  (a) a 5-membered heteroaryl ring substituted with $C_{1-6}$alkyl; or

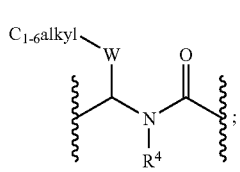

(b)

wherein W is a 5-membered heteroaryl ring, —C(O)NHNHC(O)—, —C(NH)NH—, or —C(O)NHNH—; and
$R^4$ is H or $C_{1-6}$alkyl;
or a pharmaceutically acceptable salt thereof.

In some embodiments of Formula (II), Y is CH. In certain instances, Y is N.

In some embodiments of Formula (II), $R^1$ is H or $C_{1-6}$alkyl. In certain instances, $R^1$ is $C_{1-6}$alkyl. In certain instances, $R^1$ is methyl or ethyl. In certain instances, $R^1$ is methyl. In certain instances, $R^1$ is H or methyl. In certain instances, $R^1$ is $C_{3-7}$cycloalkyl. In certain instances, $R^1$ is cyclopropyl, cyclobutyl, cyclopentyl, or cyclohexyl.

In some embodiments of Formula (II), $R^2$ is H or $C_{1-6}$alkyl. In certain instances, $R^2$ is methyl or ethyl. In certain instances, $R^2$ is H or methyl. In certain instances, $R^2$ is $C_{3-7}$cycloalkyl. In certain instances, $R^2$ is cyclopropyl, cyclobutyl, cyclopentyl, or cyclohexyl.

In some embodiments of Formula (II), each $R^3$ is independently Br, Cl, F, hydroxy, methoxy, cyano, amino, or —$CF_3$.

In some embodiments of Formula (II), n is 0 or 1. In other embodiments, n is 0.

In some embodiments of Formula (II), A moiety is a 5-membered heteroaryl ring substituted with $C_{1-6}$alkyl. In certain instances, the 5-membered heteroaryl ring contains one, two, three, or four heteroatoms selected from the group consisting of N, S, and O. In certain instances, the 5-membered heteroaryl ring contains one, two, or three heteroatoms. In certain instances, A moiety is pyrrolyl, pyrazolyl, imidazolyl, furanyl, oxazolyl, oxadiazolyl, thienyl, thiazolyl, thiadiazolyl, triazolyl, or tetrazolyl, each substituted with $C_{1-6}$alkyl. In certain instances, A moiety is imidazolyl or 1,3,4-triazolyl, each substituted with $C_{1-6}$alkyl.

In other embodiments, A moiety is

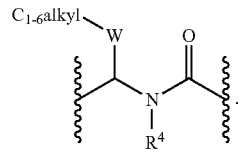

In some embodiments, W is a 5-membered heteroaryl ring. In certain instances, the 5-membered heteroaryl ring contains one, two, three, or four heteroatoms selected from the group consisting of N, S, and O. In certain instances, the 5-membered heteroaryl ring contains one, two, or three heteroatoms. In other embodiments, W is pyrrolyl, pyrazolyl, imidazolyl, furanyl, oxazolyl, oxadiazolyl, thienyl, thiazolyl, thiadiazolyl, triazolyl, or tetrazolyl. In certain instances, W is tetrazolyl, thiazolyl, thiadiazolyl, triazolyl, or oxadiazolyl, each substituted with $C_{1-6}$alkyl. In certain instances, W is tetrazolyl, thiazolyl, thiadiazolyl, triazolyl, or oxadiazolyl, and the attached $C_{1-6}$alkyl is methyl, ethyl, propyl, or butyl.

In other embodiments of Formula (II), W is —C(O)NHNHC(O)—, —C(NH)NH—, or —C(O)NHNH—.

In some embodiments of Formula (II), $R^4$ is H, methyl, ethyl, propyl, or isopropyl. In other embodiments, $R^4$ is H.

Formula III

In another aspect, the invention provides for compounds of Formula (III):

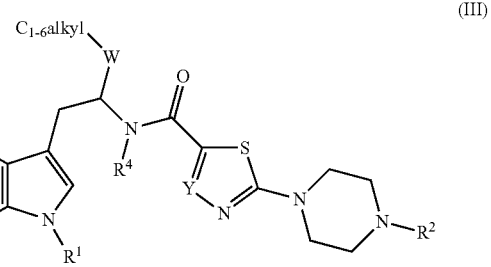

(III)

wherein
Y is CH or N;
$R^1$ is H or $C_{1-6}$alkyl;

$R^2$ is H or $C_{1-6}$alkyl;

$R^4$ is H or $C_{1-6}$alkyl; and

W is a 5-membered heteroaryl ring, —C(O)NHNH—C(O)—, —C(O)NHNH—, or —C(NH)NH—;

or a pharmaceutically acceptable salt thereof.

In some embodiments of Formula (III), W is a 5-membered heteroaryl ring. In certain instances, the 5-membered heteroaryl ring contains one, two, three, or four heteroatoms selected from the group consisting of N, S, and O. In certain instances, the 5-membered heteroaryl ring contains one, two, or three heteroatoms. In other embodiments, W is pyrrolyl, pyrazolyl, imidazolyl, furanyl, oxazolyl, oxadiazolyl, thienyl, thiazolyl, thiadiazolyl, triazolyl, or tetrazolyl. In certain instances, W is tetrazolyl, thiazolyl, thiadiazolyl, triazolyl, or oxadiazolyl, each substituted with $C_{1-6}$alkyl. In certain instances, W is tetrazolyl, thiazolyl, thiadiazolyl, triazolyl, or oxadiazolyl, and the attached $C_{1-6}$alkyl is methyl, ethyl, propyl, or butyl.

In other embodiments of Formula (III), W is —C(O)NHNHC(O)—, —C(NH)NH—, or —C(NH)NH—.

In some embodiments of Formula (III), Y is CH. In other embodiments, Y is N.

In some embodiments of Formula (III), $R^1$ is H, methyl, ethyl, propyl, or isopropyl. In other embodiments, $R^1$ is H.

In some embodiments of Formula (III), $R^2$ is H, methyl, ethyl, propyl, or isopropyl. In other embodiments, $R^2$ is H or methyl. In still other embodiments, $R^2$ is methyl.

In some embodiments of Formula (III), $R^4$ is H or methyl. In still other embodiments, $R^4$ is H.

In other embodiments, the invention is directed to a compound selected from the group consisting of:

| Ex. | Structure/Chemical Name |
|---|---|
| 1 | 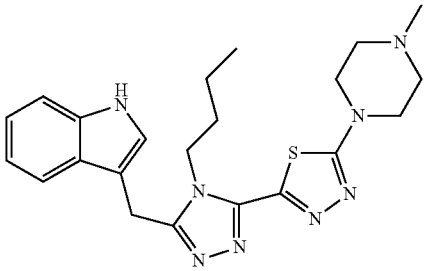 [SMILES: CCCCn1c(Cc2c[nH]c3ccccc23)nnc1-c1nnc(N2CCN(C)CC2)s1]<br>5-(5-((1H-indol-3-yl)methyl)-1-butyl-1H-imidazol-2-yl)-2-(4-methylpiperazin-1-yl)thiazole; |
| 2 | 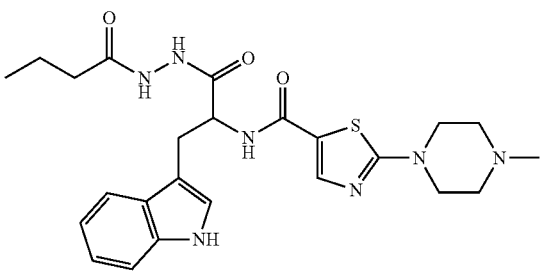 [SMILES: CCCC(=O)NNC(=O)C(Cc1c[nH]c2ccccc12)NC(=O)c1cnc(N2CCN(C)CC2)s1]<br>2-(5-((1H-indol-3-yl)methyl)-1-butyl-1H-imidazol-2-yl)-5-(4-methylpiperazin-1-yl)-1,3,4-thiadiazole; |
| 3 | 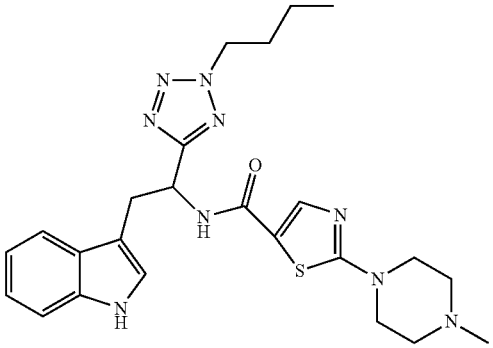 [SMILES: CCCCn1nnc(C(Cc2c[nH]c3ccccc23)NC(=O)c2cnc(N3CCN(C)CC3)s2)n1]<br>2-(5-((1H-indol-3-yl)methyl)-4-butyl-4H-1,2,4-triazol-3-yl)-5-(4-methylpiperazin-1-yl)-1,3,4-thiadiazole; |
| 4 | 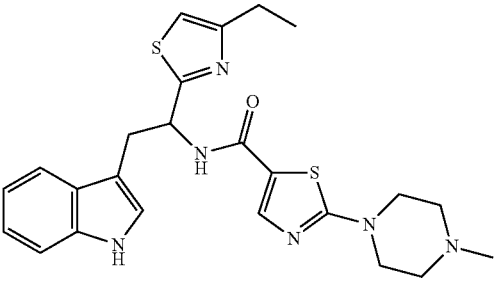 [SMILES: CCc1csc(C(Cc2c[nH]c3ccccc23)NC(=O)c2cnc(N3CCN(C)CC3)s2)n1]<br>N-(1-(2-butyrylhydrazinyl)-3-(1H-indol-3-yl)-1-oxopropan-2-yl)-2-(4-methylpiperazin-1-yl)thiazole-5-carboxamide; |
| 5 | N-(1-(2-butyl-2H-tetrazol-5-yl)-2-(1H-indol-3-yl)ethyl)-2-(4-methylpiperazin-1-yl)thiazole-5-carboxamide; |
| 6 | N-(1-(4-ethylthiazol-2-yl)-2-(1H-indol-3-yl)ethyl)-2-(4-methylpiperazin-1-yl)thiazole-5-carboxamide; |

| Ex. | Structure/Chemical Name |
|---|---|
| 7 | 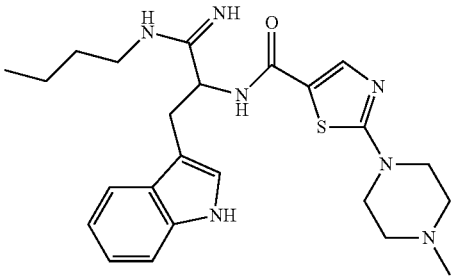 [SMILES: CCCCNC(=N)C(Cc1c[nH]c2ccccc12)NC(=O)c1cnc(N2CCN(C)CC2)s1]<br>N-(1-(butylamino)-1-imino-3-(1H-indol-3-yl)propan-2-yl)-2-(4-methylpiperazin-1-yl)thiazole-5-carboxamide; |
| 8 | 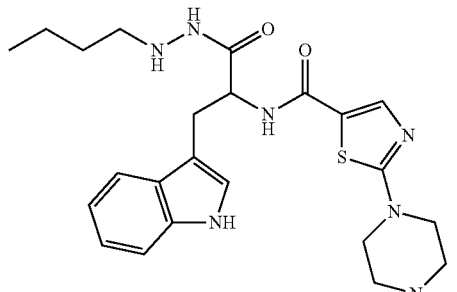<br>N-(1-(2-butylhydrazinyl)-3-(1H-indol-3-yl)-1-oxopropan-2-yl)-2-(4-methylpiperazin-1-yl)thiazole-5-carboxamide; |
| 9 | 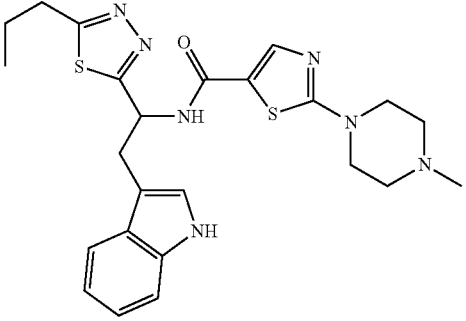 [SMILES: CCCc1nnc(C(Cc2c[nH]c3ccccc23)NC(=O)c2cnc(N3CCN(C)CC3)s2)s1]<br>N-(2-(1H-indol-3-yl)-1-(5-propyl-1,3,4-thiadiazol-2-yl)ethyl)-2-(4-methylpiperazin-1-yl)thiazole-5-carboxamide; |
| 10 | 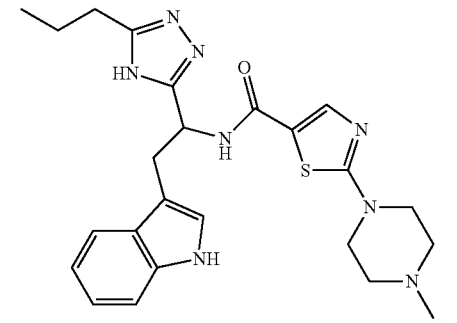 [SMILES: CCCc1nnc(C(Cc2c[nH]c3ccccc23)NC(=O)c2cnc(N3CCN(C)CC3)s2)[nH]1]<br>N-(2-(1H-indol-3-yl)-1-(5-propyl-4H-1,2,4-triazol-3-yl)ethyl)-2-(4-methylpiperazin-1-yl)thiazole-5-carboxamide; |
| 11 | 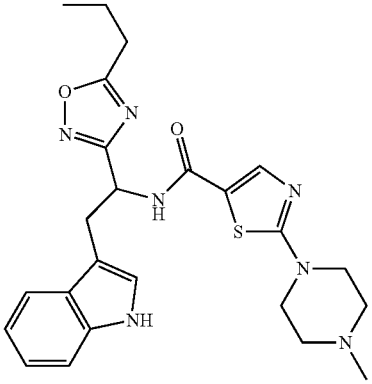 [SMILES: CCCc1nc(C(Cc2c[nH]c3ccccc23)NC(=O)c2cnc(N3CCN(C)CC3)s2)no1]<br>N-(2-(1H-indol-3-yl)-1-(5-propyl-1,2,4-oxadiazol-3-yl)ethyl)-2-(4-methylpiperazin-1-yl)thiazole-5-carboxamide; and |
| 12 | 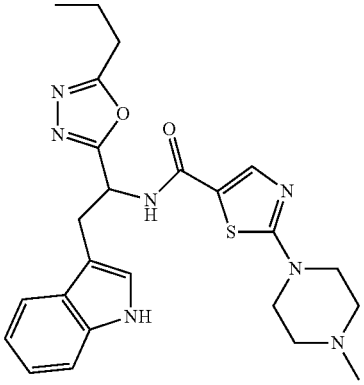 [SMILES: CCCc1nnc(C(Cc2c[nH]c3ccccc23)NC(=O)c2cnc(N3CCN(C)CC3)s2)o1]<br>N-(2-(1H-indol-3-yl)-1-(5-propyl-1,3,4-oxadiazol-2-yl)ethyl)-2-(4-methylpiperazin-1-yl)thiazole-5-carboxamide; | and pharmaceutically acceptable salts thereof.

The disclosed pharmaceutical compositions may be formulated as a pharmaceutically acceptable salt of a disclosed compound. Pharmaceutically acceptable salts are non-toxic salts of a free base form of a compound that possesses the desired pharmacological activity of the free base. These salts may be derived from inorganic or organic acids. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

General Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein, the terms "including," "containing," and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Chemical Definitions

The term "alkyl" refers to a straight- or branched-chain alkyl group having from 1 to 12 carbon atoms in the chain. Examples of alkyl groups include methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "alkoxy" refers to an alkyl group as defined above, bonded to an oxygen atom. The alkoxy group is connected to the parent structure via the oxygen atom.

The term "amino" refers to an —NH$_2$ group, or a mono- or dialkylamino group.

The term "cycloalkyl" refers to a saturated or partially saturated, monocyclic, fused polycyclic, bridged polycyclic, or spiro polycyclic carbocycle having from 3 to 12 ring atoms per carbocycle. Illustrative examples of cycloalkyl groups include the following entities, in the form of properly bonded moieties:

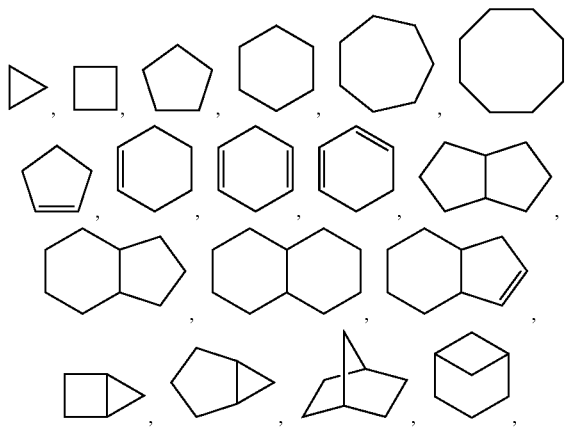

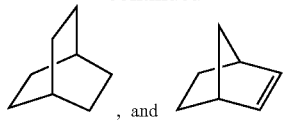
, and .

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

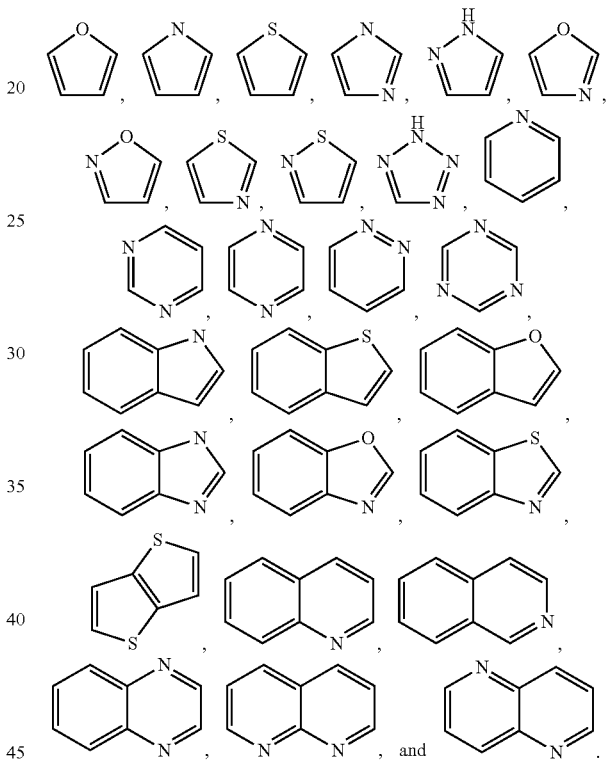

The term "halogen" represents chlorine, fluorine, bromine, or iodine. The term "halo" represents chloro, fluoro, bromo, or iodo. The term "haloalkyl" means an alkyl as defined above, substituted with one or more halogen atoms. The term "haloalkoxy" means an alkoxy as defined above, substituted with one or more halogen atoms.

Those skilled in the art will recognize that the species listed or illustrated above are not exhaustive, and that additional species within the scope of these defined terms may also be selected.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labelled compounds are useful in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

The invention also includes pharmaceutically acceptable salts of the compounds represented by Formula (I), preferably of those described above and of the specific compounds exemplified herein, and pharmaceutical compositions comprising such salts, and methods of using such salts.

A "pharmaceutically acceptable salt" is intended to mean a salt of a free acid or base of a compound represented herein that is non-toxic, biologically tolerable, or otherwise biologically suitable for administration to the subject. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates.

For a compound of Formula (I) that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

The invention also relates to pharmaceutically acceptable prodrugs of the compounds of Formula (I), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

The present invention also relates to pharmaceutically active metabolites of compounds of Formula (I), and uses of such metabolites in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini et al., J. Med. Chem. 1997, 40, 2011-2016; Shan et al., J. Pharm. Sci. 1997, 86 (7), 765-767; Bagshawe, Drug Dev. Res. 1995, 34, 220-230; Bodor, Adv. Drug Res. 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Pharmaceutical Compositions

For treatment purposes, pharmaceutical compositions comprising the compounds described herein may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the invention are sterile compositions. Pharmaceutical compositions may be prepared using compounding techniques known or that become available to those skilled in the art.

Sterile compositions are also contemplated by the invention, including compositions that are in accord with national and local regulations governing such compositions.

The pharmaceutical compositions and compounds described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the invention may be administered by a suitable route of delivery, such as oral, parenteral, rectal, nasal, topical, or ocular routes, or by inhalation. Preferably, the compositions are formulated for intravenous or oral administration.

For oral administration, the compounds the invention may be provided in a solid form, such as a tablet or capsule, or as a solution, emulsion, or suspension. To prepare the oral compositions, the compounds of the invention may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The inventive compositions may be formulated for rectal administration as a suppository. For parenteral use, including intravenous, intramuscular, intraperitoneal, intranasal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For nasal, inhaled, or oral administration, the inventive pharmaceutical compositions may be administered using, for example, a spray formulation also containing a suitable carrier.

For topical applications, the compounds of the present invention are preferably formulated as creams or ointments or a similar vehicle suitable for topical administration. For topical administration, the inventive compounds may be mixed with a pharmaceutical carrier at a concentration of about 0.1% to about 10% of drug to vehicle. Another mode of administering the agents of the invention may utilize a patch formulation to effect transdermal delivery.

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying systemic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

The term "subject" refers to a mammalian patient in need of such treatment, such as a human.

Exemplary neurodegenerative diseases that are characterized by protein aggregation include Alzheimer's Disease, Parkinson's Disease, fronto-temporal Dementia, Dementia with Lewy Bodies, PD Dementia, Multiple System Atrophy, and Amyotrophic Lateral Sclerosis.

In one aspect, the compounds and pharmaceutical compositions of the invention specifically target α-synuclein, β-amyloid, and/or tau protein aggregates. Thus, these compounds and pharmaceutical compositions can be used to prevent, reverse, slow, or inhibit aggregation of α-synuclein, β-amyloid, and/or tau proteins, and are used in methods of the invention to treat degenerative neurological diseases related to or caused by aggregation, e.g., such as aggregation of α-synuclein, β-amyloid, and/or tau proteins. Preferably, the methods of the invention target neurodegenerative diseases associated with aggregation of α-synuclein, β-amyloid, and/or tau protein. In preferred embodiments, methods of treatment target Parkinson's disease, Alzheimer's disease, Lewy body disease, or multiple system atrophy. The compounds, compositions, and method of the present invention are also used to mitigate deleterious effects that are secondary to protein aggregation, such as neuronal cell death.

In alternative aspects, the compounds, compositions, and methods of the invention are used to target synuclein aggregation. While the invention is not limited by any particular mechanism of action, synuclein aggregation is thought to be caused by a mis-alignment of the protein early in the disease process, which permits formation of protein multimers. As the number of monomer unites increases, the aggregated proteins can take on a pore-like shape, which can embed in the membrane of the neuron, disrupting ion flow and cell homeostasis.

In the inhibitory methods of the invention, an "effective amount" means an amount sufficient to reduce, slow the progression of, or reverse protein aggregation. Measuring the amount of aggregation may be performed by routine analytical methods such as those described below. Such modulation is useful in a variety of settings, including in vitro assays. In such methods, the cell is preferably a nerve cell.

In treatment methods according to the invention, an "effective amount" means an amount or dose sufficient to generally bring about the desired therapeutic benefit in subjects needing such treatment. Effective amounts or doses of the compounds of the invention may be ascertained by routine methods, such as modeling, dose escalation, or clinical trials, taking into account routine factors, e.g., the mode or route of administration or drug delivery, the pharmacokinetics of the agent, the severity and course of the infection, the subject's health status, condition, and weight, and the judgment of the treating physician. An exemplary dose is in the range of about 1 ug to 2 mg of active agent per kilogram of subject's body weight per day, preferably about 0.05 to 100 mg/kg/day, or about 1 to 35 mg/kg/day, or about 0.1 to 10 mg/kg/day. The total dosage may be given in single or divided dosage units (e.g., BID, TID, QID).

Once improvement of the patient's disease has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

Drug Combinations

The inventive compounds described herein may be used in pharmaceutical compositions or methods in combination with one or more additional active ingredients in the treatment of neurodegenerative disorders. For example, additional active ingredients are those that are known or discovered to be effective in treating neurodegenerative disorders, including those active against another target associated with the disease, such as but not limited to, a) compounds that address protein misfolding (such as drugs which reduce the production of these proteins, which increase their clearance or which alter their aggregation and/or propagation); b) compounds that treat symptoms of such disorders (e.g., dopamine replacement therapies); and c) drugs that act as neuroprotectants by complementary mechanisms (e.g., those targeting autophagy, those that are anti-oxidants, and those acting by other mechanisms such as adenosine A2A antagonists).

For example, additional active ingredients are those that are known or discovered to be effective in treating neurodegenerative disorders, including those active against another target associated with the disease, such as but not limited to, a) compounds that target different mechanisms of protein misfolding (such as aggregation and/or propagation); b) compounds that treat symptoms of such disorders (e.g., dopamine replacement therapies); and c) drugs that act as neuroprotectants by complementary mechanisms (e.g., those targeting autophagy, anti-oxidants, and adenosine A2A antagonists).

For example, compositions and formulations of the invention, as well as methods of treatment, can further comprise other drugs or pharmaceuticals, e.g., other active agents useful for treating or palliative for a degenerative neurological disease related to or caused by protein aggregation, e.g., synuclein, beta-amyloid and/or tau protein aggregation, e.g., Parkinson's disease, Alzheimer's Disease (AD), Lewy body disease (LBD) and multiple system atrophy (MSA), or related symptoms or conditions. For example, the pharmaceutical compositions of the invention may additional comprise one or more of such active agents, and methods of treatment may additionally comprise administering an effective amount of one or more of such active agents. In certain embodiments, additional active agents may be antibiotics (e.g., antibacterial or bacteriostatic peptides or proteins), e.g., those effective against gram positive or negative bacteria, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof. Additional active agents include those useful in such compositions and methods include dopamine therapy drugs, catechol-O-methyl transferase (COMT) inhibitors, monamine oxidase inhibitors, cognition enhancers (such as acetylcholinesterase inhibitors or memantine), adenosine 2A receptor antagonists, beta-secretase inhibitors, or gamma-secretase inhibitors. In particular embodiments, at least one compound of the present invention may be combined in a pharmaceutical composition or a method of treatment with one or more drugs selected from the group consisting of: tacrine (Cognex), donepezil (Aricept), rivastigmine (Exelon) galantamine (Reminyl), physostigmine, neostigmine, Icopezil (CP-118954, 5,7-dihydro-3-[2-[1-(phenylmethyl)-4-piperidinyl]ethyl]-6H-pyrrolo-[4,5-f-]-1,2-benzisoxazol-6-one maleate), ER-127528 (4-[(5,6-dimethoxy-2-fluoro-1-indanon)-2-yl]methyl-1-(3-fluorobenzyl)pipe-ridine hydrochloride), zanapezil (TAK-147; 3-[1-(phenylmethyl)piperidin-4-yl]-1-(2,3,4,5-tetrahydro-1H-1-benzazepin-8-yl)-1-propane fumarate), Metrifonate (T-588; (−)-R-.alpha.-[[2-(dimethylamino) ethoxy]methyl]benzo[b]thiophene-5-methanol hydrochloride), FK-960 (N-(4-acetyl-1-piperazinyl)-p-fluorobenzamide-hydrate), TCH-346 (N-methyl-N-2-pyropinyldibenz [b,f]oxepine-10-methanamine), SDZ-220-581 ((S)-.alpha.-amino-5-(phosphonomethyl)-[1,1'-biphenyl]-3-propionic acid), memantine (Namenda/Exiba) and 1,3,3,5,5-pentamethylcyclohexan-1-amine (Neramexane), tarenflurbil (Flurizan), tramiprosate (Alzhemed), clioquinol, PBT-2 (an 8-hydroxyquinilone derivative), 1-(2-(2-Naphthyl)ethyl)-4-(3-trifluoromethylphenyl)-1,2,3,6-tetrahydropyr-idine, Huperzine A, posatirelin, leuprolide or derivatives thereof, ispronicline, (3-aminopropyl)(n-butyl)phosphinic acid (SGS-742), N-methyl-5-(3-(5-isopropoxypyridinyl))-4-penten-2-amine (ispronicline), 1-decanaminium, N-(2-hydroxy-3-sulfopropyl)-N-methyl-N-octyl-, inner salt (zt-1), salicylates, aspirin, amoxiprin, benorilate, choline magnesium salicylate, diflunisal, faislamine, methyl salicylate, magnesium salicylate, salicyl salicylate, diclofenac, aceclofenac, acemetacin, bromfenac, etodolac, indometacin, nabumetone, sulindac, tolmetin, ibuprofen, carprofen, fenbufen, fenoprofen, flurbiprofen, ketoprofen, ketorolac, loxoprofen, naproxen, tiaprofenic acid, suprofen, mefenamic acid, meclofenamic acid, phenylbutazone, azapropazone, metamizole, oxyphenbutazone, sulfinprazone, piroxicam, lornoxicam, meloxicam, tenoxicam, celecoxib, etoricoxib, lumiracoxib, parecoxib, rofecoxib, valdecoxib, nimesulide, arylalkanoic acids, 2-arylpropionic acids (profens), N-arylanthranilic acids (fenamic acids), pyrazolidine derivatives, oxicams, COX-2 inhibitors, sulphonanilides, essential fatty acids, and Minozac (2-(4-(4-methyl-6-phenylpyridazin-3-yl) piperazin-1-yl)pyrimidine dihydrochloride hydrate), or a combination thereof. Such a combination may serve to increase efficacy, ameliorate other disease symptoms, decrease one or more side effects, or decrease the required dose of an inventive compound. The additional active ingredients may be administered in a separate pharmaceutical composition from a compound of the present invention or may be included with a compound of the present invention in a single pharmaceutical composition. The additional active ingredients may be administered simultaneously with, prior to, or after administration of a compound of the present invention.

Chemical Synthesis

Exemplary chemical entities useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used. Unless otherwise specified, the variables are as defined above in reference to Formula (I).

EXAMPLES

The following examples are offered to illustrate but not to limit the invention. One of skill in the art will recognize that the following synthetic reactions and schemes may be modified by choice of suitable starting materials and reagents in order to access other compounds of Formula (I).

Example 1

5-(5-((1H-indol-3-yl)methyl)-1-butyl-1H-imidazol-2-yl)-2-(4-methylpiperazin-1-yl)thiazole

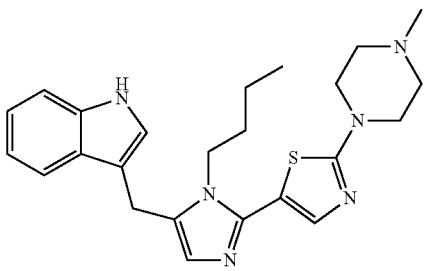 [SMILES: CCCCn1c(Cc2c[nH]c3ccccc23)cnc1-c1cnc(N2CCN(C)CC2)s1]

Step 1. General Procedure for Preparation of Intermediate 2.

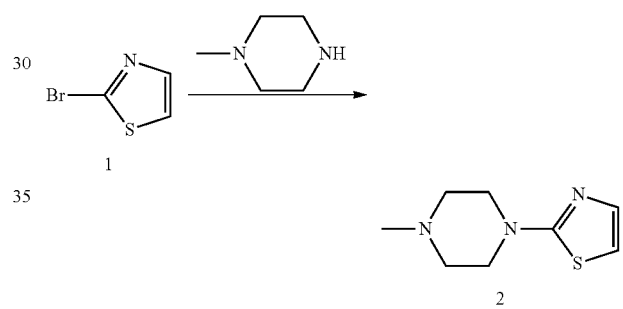

A solution of Intermediate 1 (164.0 g, 1 mol), methylpiperazine (100.0 g, 1 mol), and $K_2CO_3$ (414.0 g, 3 mol) in DMF (1650 mL) was stirred at 140° C. for 12 h. TLC $R_f$ 0.2 ($CH_2Cl_2$/MeOH, 10:1) showed the reaction was complete. The reaction mixture was concentrated and the residue was partitioned between EtOAc and water. The organic layer was dried over $Na_2SO_4$, filtered and concentrated. The residue was purified by column chromatography ($CH_2Cl_2$/MeOH, 50:1) to give Intermediate 2 (120 g, 66%) as yellow oil. $^1$H NMR (400 MHz $CDCl_3$) δ 2.35 (s, 3H), 2.51-2.54 (m, 4H), 3.50-3.53 (m, 4H), 6.56 (d, J=3.6 Hz, 1H), 7.19 (d, J=3.6 Hz, 1H).

Step 2. General Procedure for Preparation of Intermediate 3.

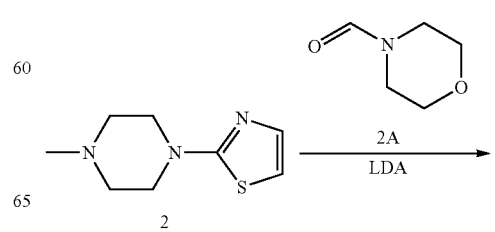

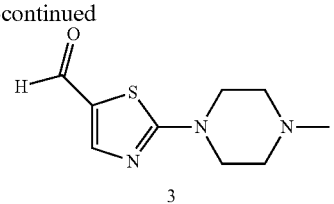

To a solution of diisopropylamine (27 g, 0.27 mol) in THF (250 mL) was added n-BuLi (117 mL, 0.27 mol) at −78° C. under N₂. The mixture was slowly warmly to 0° C. Intermediate 2 (33 g, 0.18 mol) in THF (250 mL) was added dropwise at −78° C. for 1 h. Then compound 2A (31 g, 0.27 mol) in THF (250 mL) was added dropwise at −78° C. for 30 min. The mixture was stirred at −30° C. for 1 h. The reaction mixture was quenched with saturated NH₄Cl, and the residue was partitioned between EtOAc and water. The organic layer was dried over Na₂SO₄, concentrated and the residue was purified by column chromatography (CH₂Cl₂/MeOH, 100:1) to give Intermediate 3 (17 g, 45%) as a yellow solid. ¹H NMR (400 MHz, MeOD) δ 2.35 (s, 3H), 2.55-2.57 (m, 4H), 3.60-3.68 (m, 4H), 8.00 (s, 1H), 9.63 (s, 1H).

Step 3. General Procedure for Preparation of Intermediate 4.

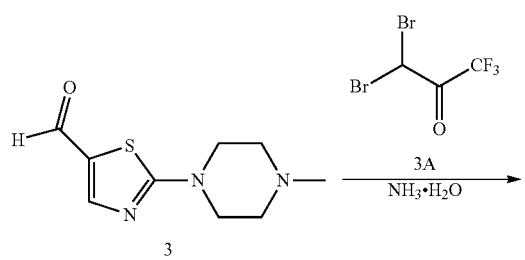

To a solution of NaOAc (19.1 g, 0.23 mol) in H₂O (125 mL) was added compound 3A (33 g, 0.13 mol) at room temperature. Then the mixture was stirred at reflux for 30 min. After cooling to rt, the mixture was added to a solution of Intermediate 3 (24.6 g, 0.12 mol) in the mixture of MeOH (375 mL) and NH₃·H₂O (138 mL) at 0° C. The mixture was stirred at rt for 36 h. TLC R_f 0.2 (CH₂Cl₂/MeOH, 10:1) showed the reaction was complete. The reaction mixture was concentrated and the residue was partitioned between EtOAc and water. The organic layer was dried over Na₂SO₄, concentrated and the residue was purified by column chromatography (CH₂Cl₂/MeOH, 50:1) to give Intermediate 4 (7.4 g, 20%) as a yellow solid. ¹H NMR (400 MHz, MeOD) δ 2.35 (s, 3H), 2.56-2.58 (m, 4H), 3.55-3.57 (m, 4H), 7.56 (s, 1H), 7.61 (s, 1H).

Step 4. General Procedure for Preparation of Intermediate 5.

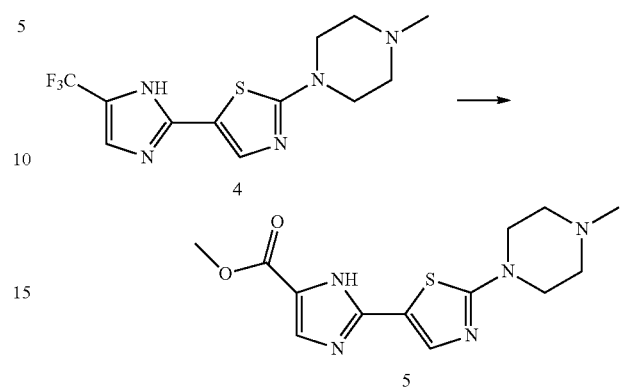

To a solution of Intermediate 4 (6 g, 19 mmol) in MeOH (46 mL) and H₂O (1.6 mL) was added NaOMe (6 g, 0.11 mol) at room temperature. Then the mixture was stirred at 70° C. under N₂ for 12 h. TLC R_f 0.4 (CH₂Cl₂/MeOH, 10:1) showed the reaction was complete. Then the mixture was adjusted to pH=1 with conc. HCl and stirred for 2 h. The mixture was adjusted to pH=9 with NaHCO₃ at 0° C. Then the mixture was concentrated to remove MeOH and the solid was collected and dried to give Intermediate 5 (4.6 g, 80%) as a yellow solid.

Step 5. General Procedure for Preparation of Intermediate 6.

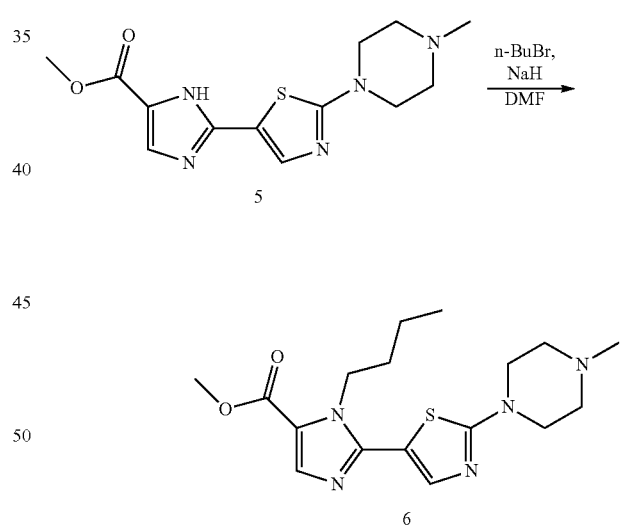

To a solution of Intermediate 5 (7 g, 22.8 mmol) in DMF (40 mL) was added NaH (1.36 g, 34.2 mmol) and n-BuI (4.2 g, 22.8 mmol) at 0° C. Then the mixture was stirred at rt for 18 h. TLC R_f 0.6 (CH₂Cl₂/MeOH, 10:1) showed the reaction was complete. The reaction mixture was concentrated and the residue was partitioned between EtOAc and water. The organic layer was dried over Na₂SO₄, concentrated and the residue was purified by preparatory HPLC to give Intermediate 6 (0.3 g, 4%) as a white solid. ¹H NMR (400 MHz, MeOD) δ 0.95 (t, J=7.6 Hz, 3H), 1.38 (t, J=7.6 Hz, 3H), 1.75 (t, J=8.0 Hz, 3H), 2.36 (s, 3H), 2.56-2.60 (m, 4H), 3.57-3.60 (m, 4H), 3.86 (s, 3H), 4.80 (m, 4H), 7.52 (m 1H), 7.71 (s, 1H).

Step 6. General Procedure for Preparation of Intermediate 7.

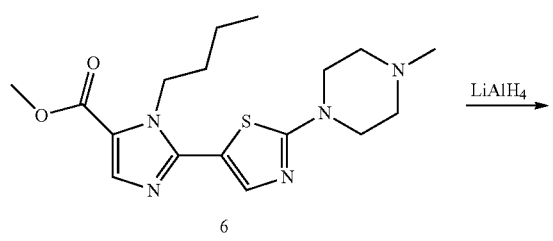

To a solution of LiAlH₄ (0.5 g, 13.5 mmol) in THF (5 mL) was added Intermediate 6 (0.2 g, 0.55 mmol) in THF (3 mL) dropwise at 0° C. under N₂. After addition was complete, the reaction mixture was stirred at 25° C. for 12 h. TLC $R_f$ 0.2 (CH₂Cl₂/MeOH, 10:1) showed the reaction was complete. The reaction mixture was cooled to −10° C. and 5% NaOH (2 mL) was added dropwise. Then the solution was filtered and concentrated to give Intermediate 7 (0.18 g, 97%) as a yellow solid, which was used directly without purification.

Step 7. General Procedure for Preparation of Example 1.

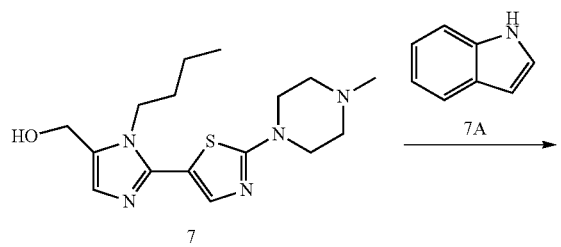

To a solution of Intermediate 7 (0.18 g, 0.54 mmol) and compound 7A (0.13 g, 1 mmol) in DCE (6 mL) was added TFA (0.15 mL). After addition, the reaction mixture was stirred at 50° C. for 12 h. TLC $R_f$ 0.4 (CH₂Cl₂/MeOH, 10:1) showed the reaction was complete. The reaction mixture was washed with saturated NaHCO₃ and extracted with EtOAc. The organic layer was washed with brine, dried with Na₂SO₄ and concentrated. The residue was purified by column chromatography (CH₂Cl₂/MeOH, 50:1) to give the title compound (0.07 g, 30%) as a light yellow solid. ¹H NMR (400 MHz, CDCl₃) δ 0.75-0.79 (m, 3H), 1.15-1.25 (m, 2H), 1.48-1.56 (m, 2H), 2.30 (s, 3H), 2.48-2.51 (m, 4H), 3.49-3.51 (m, 4H), 3.82-3.86 (m, 2H), 4.00 (s, 2H), 6.81 (s, 1H), 6.86 (s, 1H), 7.04-7.51 (m, 5H), 8.19 (s, 1H). MS: (M+1⁺): 435.3.

Example 2

2-(5-((1H-indol-3-yl)methyl)-1-butyl-1H-imidazol-2-yl)-5-(4-methylpiperazin-1-yl)-1,3,4-thiadiazole

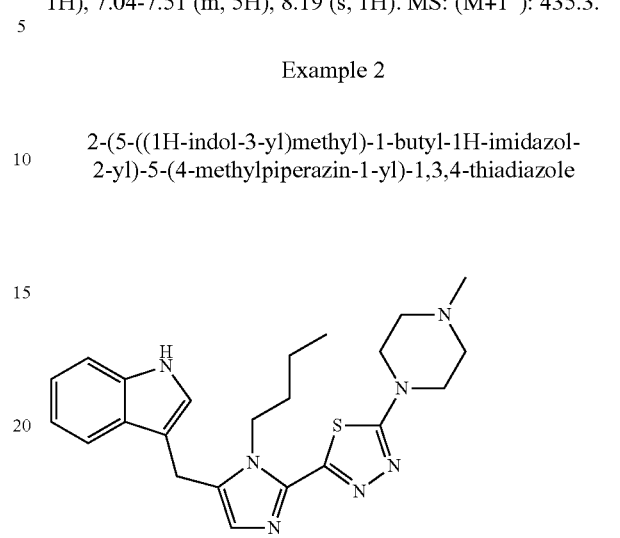

Step 1. General Procedure for Preparation of Intermediate 8.

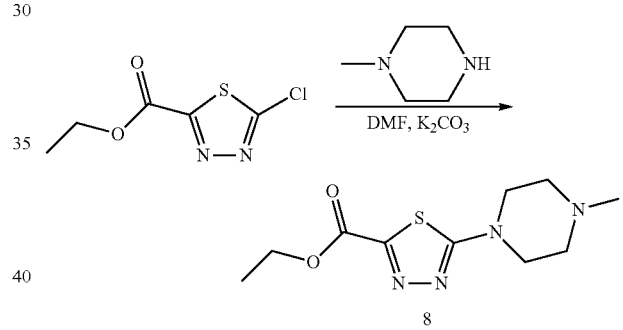

A solution of ethyl 5-chloro-1,3,4-thiadiazole-2-carboxylate (60 g, 0.313 mol), K₂CO₃ (130 g, 0.94 mol) and methyl piperazine in DMF (300 mL) was stirred at 40° C. for 3 h. TLC $R_f$ 0.5 (petroleum ether/EtOAc, 10/1) showed the reaction was complete. The reaction mixture was poured into water and extracted with. CH₂Cl₂. The organic layer was washed with water, dried over Na₂SO₄, and concentrated to give Intermediate 8 (58.5 g, 73%) as a yellow solid. ¹H NMR (400 MHz, CDCl₃) δ 1.35-1.47 (m, 3H), 2.34 (s, 3H), 2.47-2.60 (m, 4H), 3.60-3.71 (m, 4H), 4.37-4.47 (m, 2H), 5.30 (s, 1H).

Step 2. General Procedure for Preparation of Intermediate 9.

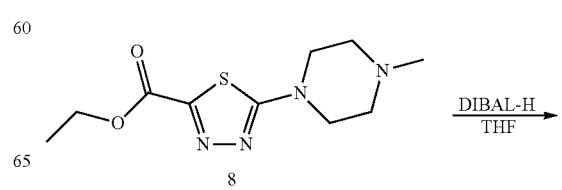

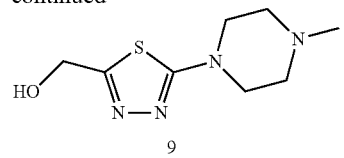

9

To a solution of Intermediate 8 (40 g, 0.156 mol) in THF (400 mL) was added dropwise DIBAL-H (313 mL) at −78° C., stirred at 0° C. for 2 h, and stirred at room temperature for another 3 h. TLC R$_f$ 0.8 (CH$_2$Cl$_2$/MeOH, 10/1) showed the reaction was complete. The reaction mixture was quenched with water (12.5 mL), 15% NaOH (12.5 mL) and water (31.3 mL) in turn. The mixture was filtered and collected the filtration, which was concentrated to obtain the crude product. The crude product was purified by column chromatography to give Intermediate 9 (20 g, 60%) as a yellow solid. $^1$H NMR (400 MHz, DMSO) δ 2.33 (s, 3H), 2.51-2.58 (m, 4H), 3.39-3.49 (m, 4H), 3.88 (s, 1H), 4.84 (s, 2H).

Step 3. General Procedure for Preparation of Intermediate 10.

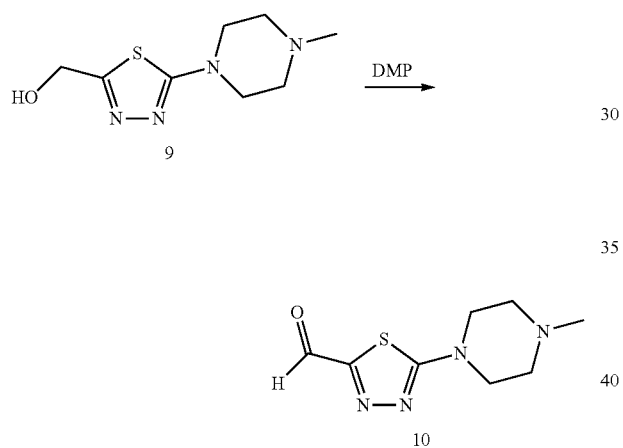

To a solution of Intermediate 9 (30 g, 0.14 mol) in CH$_2$Cl$_2$ (300 mL), Dess-Martin periodinane (119 g, 0.28 mol) was added at −78° C. The mixture was warmed slowly to room temperature, stirred for 5 h more. TLC R$_f$ 0.4 (CH$_2$Cl$_2$/MeOH, 10:1) showed the reaction was complete. The reaction mixture was quenched by NaCO$_3$ solution, extracted with EtOAc, washed with brine, dried over Na$_2$SO$_4$, and concentrated to give Intermediate 10 (22.5 g, 76%) as a yellow solid. $^1$H NMR (400 MHz, CDCl$_3$) δ 2.39-2.44 (s, 3H), 2.64-2.70 (m, 4H), 3.73-3.75 (m, 4H).

Step 4. General Procedure for Preparation of Intermediate 11.

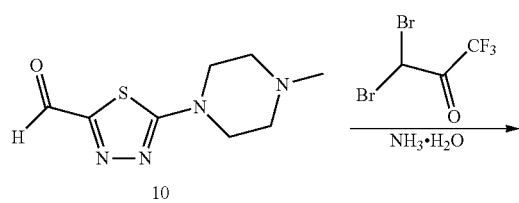

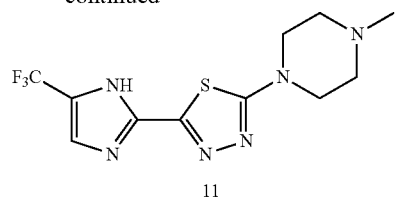

11

To a solution of NaOAc (21.2 g, 0.265 mol) in H$_2$O (150 mL) was added 1,1-dibromo-3,3,3-trifluoracetone (37 g, 0.138 mol) at room temperature. Then the mixture was refluxed for 30 min. After cooling to room temperature, the mixture was added to a solution of Intermediate 10 (22.5 g, 0.106 mol) in MeOH (450 mL) and NH$_3$—H$_2$O (150 mL) at 0° C. The mixture was stirred at room temperature for 48 h. TLC R$_f$ 0.5 (CH$_2$Cl$_2$/MeOH, 15:1) showed the reaction was complete. The reaction mixture was concentrated and the residue was portioned between EtOAc and water. The organic layer was dried over Na$_2$SO$_4$, concentrated and the residue was purified by column chromatography (CH$_2$Cl$_2$/MeOH, 50:1) to give Intermediate 11 (7.5 g, 22%) as a yellow solid. $^1$H NMR (400 MHz, DMSO) δ 2.22 (s, 3H), 2.41-2.49 (m, 4H), 3.51-3.53 (m, 4H), 7.92 (s, 1H).

Step 5. General Procedure for Preparation of Intermediate 12.

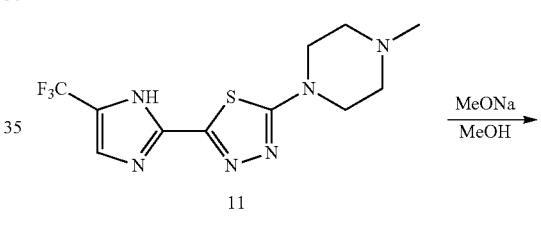

12

To a solution of Intermediate 11 (16.7 g, 31 mmol) in MeOH (124 mL) and H$_2$O (2.8 mL) was added NaOMe (6 g, 0.11 mol) at room temperature. Then the mixture was stirred at 70° C. under N$_2$ overnight. TLC R$_f$ 0.4 (CH$_2$Cl$_2$/MeOH, 10/1) showed the reaction was complete. Then the mixture was adjusted to pH=1 with conc. HCl and stirred for 2 h. The mixture was adjusted to pH=9 with NaHCO$_3$ solution at room temperature. Then the mixture was concentrated to remove MeOH and the solid was collected, washed with CH$_2$Cl$_2$, and dried to give Intermediate 12 (8.2 g, 82%) as a yellow solid. $^1$H NMR (400 MHz, DMSO) δ 2.2 (s, 3H), 2.42-2.44 (m, 4H), 3.43-3.49 (m, 4H), 3.70 (s, 3H), 7.76 (s, 1H).

Step 6. General Procedure for Preparation of Intermediate 13.

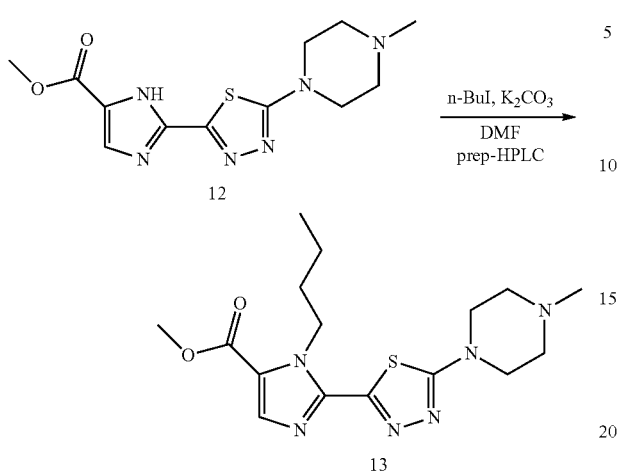

To a solution of Intermediate 12 (7.7 g, 25 mmol) in DMF (80 mL) was added K₂CO₃ (4.14 g, 0.03 mol) and n-BuI (5.52 g, 30 mmol), stirred at room temperature for 3 h. TLC R$_f$ 0.3 (CH$_2$Cl$_2$/MeOH, 10:1) showed the reaction was complete. The reaction mixture was poured into water and extracted with CH$_2$Cl$_2$. The organic layer was dried over Na$_2$SO$_4$, concentrated and the residue was purified by prep-HPLC to give Intermediate 13 (0.65 g, 15%) as a white solid. $^1$H NMR (400 MHz, CDCl$_3$) δ 0.81-0.88 (m, 3H), 1.30-1.39 (m, 2H), 1.70-1.77 (m, 2H), 2.29 (s, 3H), 2.43-2.50 (m, 4H), 3.56-3.62 (m, 4H), 3.81 (s, 3H), 4.84-4.88 (m, 2H), 7.69 (s 1H).

Step 7. General Procedure for Preparation of Intermediate 14.

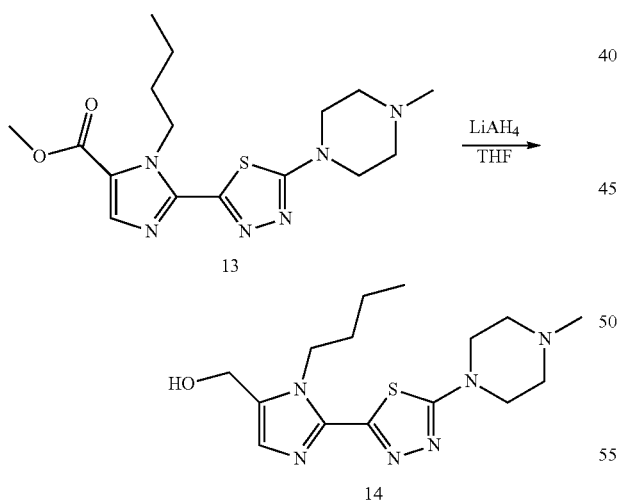

To a solution of LiAlH$_4$ (274 mg, 7.2 mmol) in THF (30 mL), Intermediate 13 (1.3 g, 3.6 mmol) in THF (30 mL) was added dropwise at 0° C. under N$_2$. After addition, the reaction mixture was stirred at 25° C. for 3 h. TLC R$_f$ 0.6 (CH$_2$Cl$_2$/MeOH, 10:1) showed the reaction was complete. The reaction mixture was quenched with water (0.3 mL), 15% NaOH (0.3 mL) and water (0.9 mL) in turn. The mixture was filtered and the filtration was concentrated to give Intermediate 14 (1.0 g, 83%) as a white solid. $^1$H NMR (400 MHz, MeOD) δ 0.94-0.95 (m, 3H), 1.37-0.44 (m, 2H), 1.77-1.85 (m, 2H), 2.36 (s, 3H), 2.59-2.61 (m, 4H), 3.60-3.62 (m, 4H), 4.51-4.55 (m, 2H), 4.64 (s, 2H), 7.04 (s 1H).

Step 8. General Procedure for Preparation of Example 2.

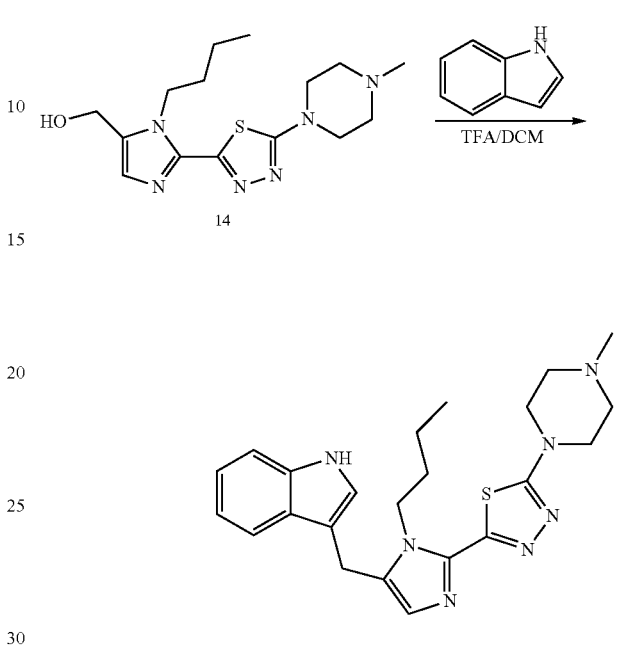

To a solution of Intermediate 14 (1.0 g, 3.0 mmol) and indole (702 mg, 6.0 mmol) in DCE (20 mL) was added TFA (1.0 mL). After addition, the reaction mixture was stirred at 80° C. overnight. TLC R$_f$ 0.4 (CH$_2$Cl$_2$/MeOH, 10:1) showed the reaction was complete. The reaction mixture was washed with NaHCO$_3$ solution and extracted with CH$_2$Cl$_2$. The organic layer was washed with brine, dried over Na$_2$SO$_4$ and concentrated. The residue was purified by prep-HPLC to give the title compound (240 mg, 18%) as a white solid. $^1$H NMR (400 MHz, MeOD) δ 0.75-0.79 (m, 3H), 1.20-1.25 (m, 2H), 1.46-1.48 (m, 2H), 2.74 (s, 3H), 3.16 (s, 4H), 3.76 (s, 4H), 4.14 (s, 2H), 4.34-4.38 (s, 2H), 6.83 (s, 1H), 6.94 (s, 1H), 7.05 (d, J=6.0 Hz, 1H), 7.32 (s, 1H), 7.42 (d, J=8.0 Hz, 1H). MS: (M+1$^+$): 436.3.

Example 3

2-(5-((1H-indol-3-yl)methyl)-4-butyl-4H-1,2,4-triazol-3-yl)-5-(4-methylpiperazin-1-yl)-1,3,4-thiadiazole

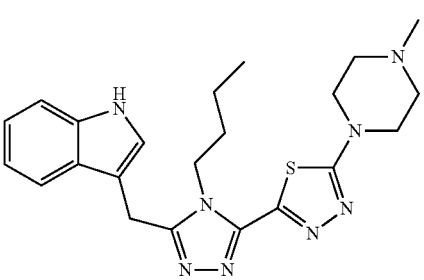 [SMILES: CCCCn1c(Cc2c[nH]c3ccccc23)nnc1-c1nnc(N2CCN(C)CC2)s1]

Step 1. General Procedure for Preparation of Intermediate 15.

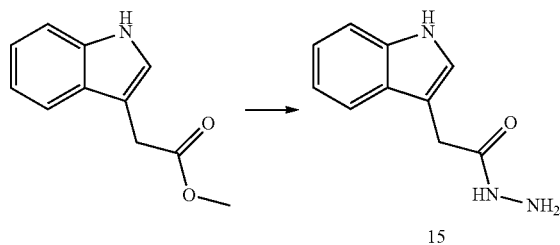

A solution of methyl 2-(1H-indol-3-yl)acetate (20.0 g, 0.106 mol), and NH$_2$NH$_2$.H$_2$O (12.5 g, 0.53 mol) in MeOH (200 mL) was stirred at 60° C. overnight. TLC R$_f$ 0.5 (petroleum ether/EtOAc, 4/1) showed the reaction was complete. The reaction mixture was concentrated and CH$_2$Cl$_2$ was added to the residue to recrystallize the product. The mixture was filtered and the filter cake was dried by vacuum at 50° C. to give Intermediate 15 (20 g, 100%) as yellow solid. $^1$H NMR (400 MHz, MeOD) δ 3.61 (s, 2H), 6.99-7.02 (m, 1H), 7.07-7.11 (m, 1H), 7.15 (s, 1H), 7.32-7.34 (d, J=8.4 Hz, 1H), 7.53-7.55 (d, J=8.0 Hz, 1H).

Step 2. General Procedure for Preparation of Intermediate 16.

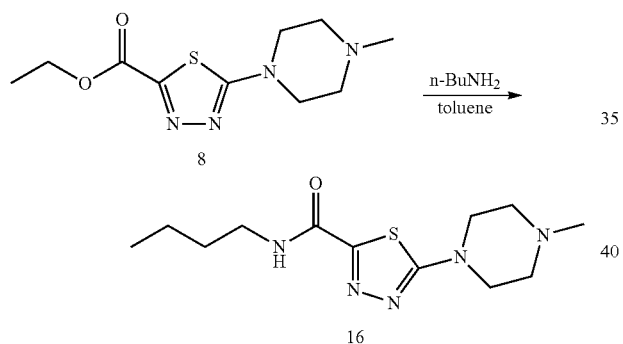

A solution of Intermediate 8 (4.5 g, 17.6 mmol) and n-BuNH$_2$ (5.14 g, 70.32 mmol) in toluene was stirred at 160° C. in sealed tube for 4 h. TLC R$_f$ 0.6 (CH$_2$Cl$_2$/MeOH, 15:1) showed the reaction was complete. The reaction mixture was concentrated at 60° C. in vacuum to give Intermediate 16 (4.2 g, 84%) as a yellow solid, which was used for next step without further purification. $^1$H NMR (400 MHz, CDCl$_3$) δ 0.91-0.95 (m, 3H), 1.35-1.44 (m, 2H), 1.55-1.62 (m, 2H), 2.34-2.36 (s, 3H), 2.52-2.53 (m, 4H), 3.39-3.44 (m, 2H), 3.60-3.73 (m, 4H), 7.06 (s, 1H).

Step 3. General Procedure for Preparation of Intermediate 17.

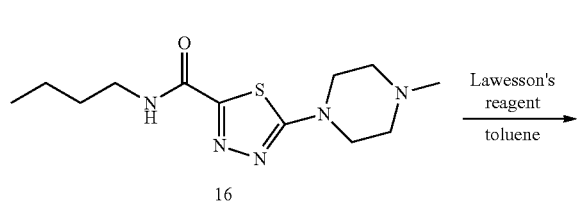

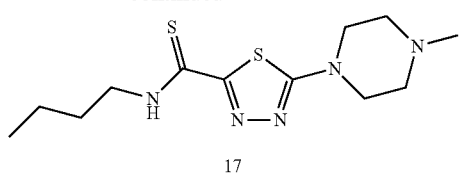

A solution of Intermediate 16 (16.8 g, 0.059 mmol) and Lawesson's reagent (21.7 g, 0.059 mmol) in toluene (170 mL) was stirred at 110° C. for 12 h. TLC R$_f$ 0.5 (CH$_2$Cl$_2$/MeOH, 10:1) showed the reaction was complete. Then the mixture was concentrated and the residue was dissolved in CH$_2$Cl$_2$. The organic layer was washed with NaHCO$_3$ solution, brine, dried over Na$_2$SO$_4$ and concentrated. The crude product was purified by column chromatography (CH$_2$Cl$_2$/MeOH, 100/1) to give Intermediate 17 (15.2 g, 86%) as a light yellow solid. $^1$H NMR (400 MHz, CDCl$_3$) δ 0.82-0.92 (m, 3H), 1.33-1.42 (m, 2H), 1.61-1.69 (m, 2H), 2.34 (s, 3H), 2.54 (s, 4H), 3.57-3.60 (m, 4H), 3.67-3.75 (m, 2H), 6.73 (s, 1H).

Step 4. General Procedure for Preparation of Intermediate 18.

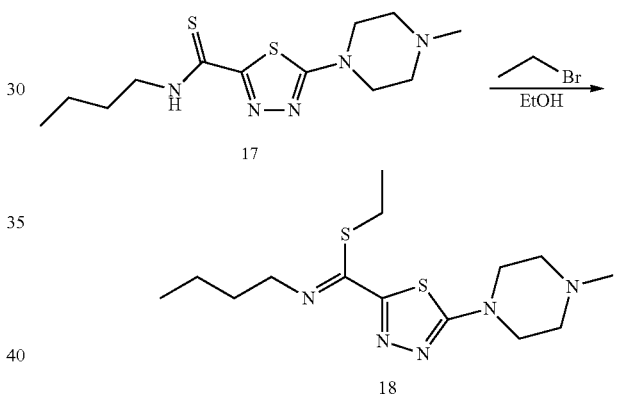

To a solution of EtONa (2.4 g, 8.0 mmol) in EtOH (64 mL), Intermediate 17, and ethyl bromide was added. The mixture was stirred at 50° C. overnight. Analysis by LC/MS showed the reaction was complete. Then the mixture was concentrated and the residue was dissolved in CH$_2$Cl$_2$. The organic layer was washed with water, brine, dried over Na$_2$SO$_4$ and concentrated to give Intermediate 18 (2.1 g, 81%) as a light yellow solid. $^1$H NMR (400 MHz, MeOD) δ 0.92-0.95 (m, 3H), 1.24-1.27 (m, 3H), 1.40-1.41 (m, 2H), 1.66-1.70 (m, 2H), 2.33 (s, 3H), 2.50-2.52 (m, 4H), 3.43-3.44 (m, 2H), 3.58-3.63 (m, 6H).

Step 5. General Procedure for Preparation of Example 3.

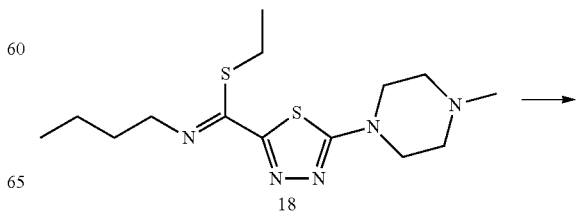

33
-continued

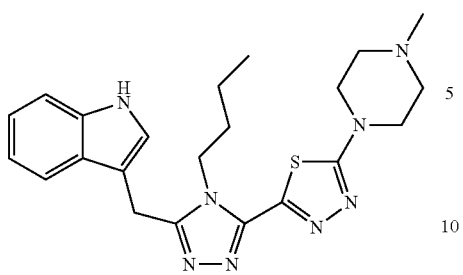

A solution of Intermediate 18 (2.1 g, 1.94 mmol) and Intermediate 15 (3.5 g, 1.94 mmol) in n-BuOH (20 mL) was stirred at 120° C. for 5 h. TLC $R_f$ 0.6 ($CH_2Cl_2$/MeOH, 10:1) showed the reaction was complete. The reaction mixture was concentrated and purified by column chromatography ($CH_2Cl_2$/MeOH, 50:1) to give the crude product. Then the crude product was purified by prep-HPLC to give the title compound (169 mg, 6%) as a yellow solid. $^1$H NMR (400 MHz, MeOD) δ 0.58-0.62 (m, 3H), 1.06-1.07 (m, 2H), 1.11-1.19 (m, 2H), 2.30 (s, 3H), 2.56-2.58 (m, 4H), 3.55-3.57 (m, 4H), 4.20-4.23 (m, 2H), 4.34 (s, 2H), 6.88-6.92 (m, 1H), 6.99-7.03 (m, 1H), 7.08 (s, 1H), 7.26-7.28 (m, 1H), 7.39-7.41 (m, 1H). MS: (M+1$^+$): 437.3.

Example 4

N-(1-(2-butyrylhydrazinyl)-3-(1H-indol-3-yl)-1-oxopropan-2-yl)-2-(4-methylpiperazin-1-yl)thiazole-5-carboxamide

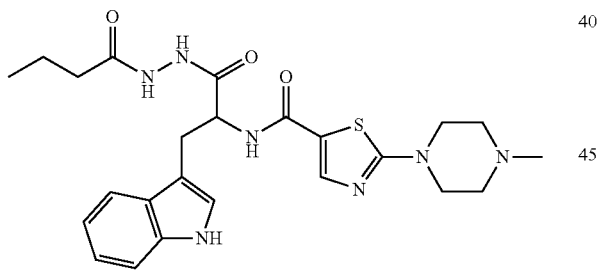

The title compound may be prepared according to the following scheme.

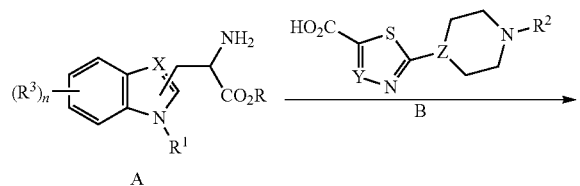

34
-continued

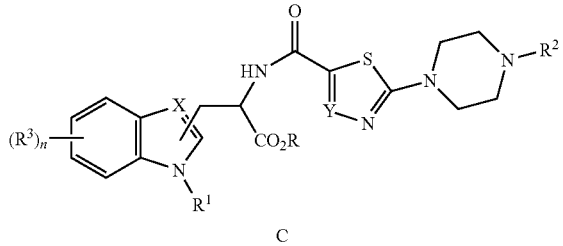

C

Compounds A are commercially available, for example, tryptophan and substituted tryptophan derivatives. The acid group of compounds A, in which R is H, may be protected as an ester or other carboxylic acid equivalent. Coupling of amines A with aryl acids B under amide coupling conditions provides amides C. Aryl acids B are available using methods analogous to those described above for Intermediate 8 and suitable ester hydrolysis methods known in the art. Additional methods for preparing intermediates in the synthesis of compounds of Formula (I) are described in PCT Intl. Pat. Publ. WO2011/084642, which is incorporated herein by reference. The —$CO_2R$ moiety in compound C may be converted back to an acid group, and coupled with a $C_{1-6}$alkyl acyl hydrazide under amide coupling conditions to form Example 4.

Example 5

N-(1-(2-butyl-2H-tetrazol-5-yl)-2-(1H-indol-3-yl)ethyl)-2-(4-methylpiperazin-1-yl)thiazole-5-carboxamide

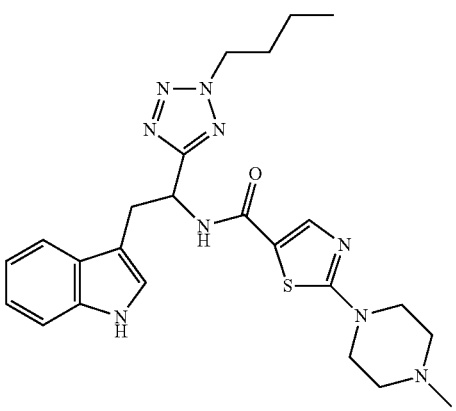 [SMILES: CCCCn1nnc(C(Cc2c[nH]c3ccccc23)NC(=O)c2cnc(N3CCN(C)CC3)s2)n1]

The compounds of Example 5 and Examples 6, 9, and 11-12 (see below) may be prepared as shown in Example 4, but then converting the acid of compound C into the desired $C_{1-6}$alkyl substituted heteroaryl moiety using cyclization methods known to one of ordinary skill in the art. Suitable methods for forming such heteroaryl groups are described in Streitweiser, Jr., A. et al., Introduction to Organic Chemistry, 3$^{rd}$ ed., 1985, Chapter 31; Joule, J. A. et al., Heterocyclic Chemistry, 3$^{rd}$ ed., 1995; Bartlett, R. K. et al., J. Chem. Soc. Soc., C. 1967, 1664; Wadsworth, H. J. et al. J. Med. Chem. 1992, 35, 1280; Finnegan, W. G. et al., J. Am. Chem. Soc. 1958, 80, 3908; Goddard, C. J. J. Het. Chem. 1991, 28, 17-28; Clapp, L. B., "1,2,4-Oxadiazoles," in Advances in Heterocyclic Chemistry, vol. 20, 1976, 65. Additional cyclization methods are shown in Examples 1-3. Representative methods include Robinson-Gabriel cyclization or Hantzsch synthesis to form an oxazole, reaction of an ester with an oxime or hydrazone to form 1,2-azoles, reaction of a nitrile under Pinner conditions to form a triazole, or with NaN₃ to form a tetrazole, or with hydroxylamine followed by an acid chloride to form an oxadiazole. For example, the compound of Example 4 may be reacted with a suitable amine and cyclized to form a triazole.

Example 6

N-(1-(4-ethylthiazol-2-yl)-2-(1H-indol-3-yl)ethyl)-2-(4-methylpiperazin-1-yl)thiazole-5-carboxamide

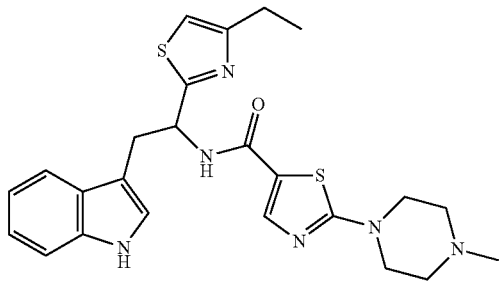 [SMILES: CCc1csc(C(Cc2c[nH]c3ccccc23)NC(=O)c2cnc(N3CCN(C)CC3)s2)n1]

See description for Example 5.

Example 7

N-(1-(butylamino)-1-imino-3-(1H-indol-3-yl)propan-2-yl)-2-(4-methylpiperazin-1-yl)thiazole-5-carboxamide

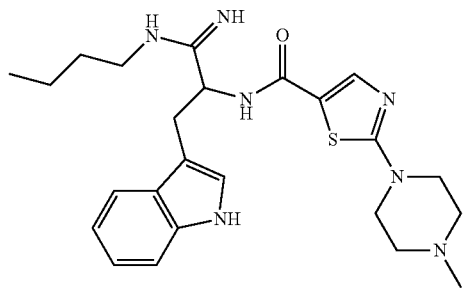 [SMILES: CCCCNC(=N)C(Cc1c[nH]c2ccccc12)NC(=O)c1cnc(N2CCN(C)CC2)s1]

Example 7 may be prepared as shown for Example 4, but reacting the resulting acid C with $C_{1-6}$alkylNH₂, followed by NH₃, to form the amidine of Example 7.

Example 8

N-(1-(2-butylhydrazinyl)-3-(1H-indol-3-yl)-1-oxopropan-2-yl)-2-(4-methylpiperazin-1-yl)thiazole-5-carboxamide

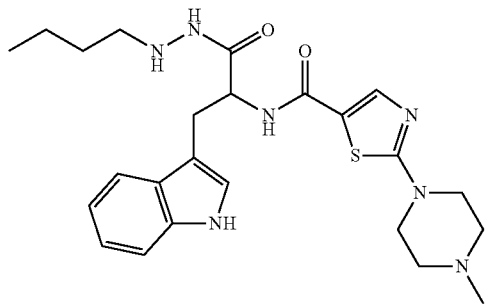 [SMILES: CCCCNNC(=O)C(Cc1c[nH]c2ccccc12)NC(=O)c1cnc(N2CCN(C)CC2)s1]

Example 8 may be prepared according to the scheme shown in Example 4, but reacting the acid C or its ester analog with a $C_{1-6}$alkylhydrazine under amide coupling conditions. For example, the compound may be prepared using methods analogous to those described for the preparation of Intermediate 15.

Example 9

N-(2-(1H-indol-3-yl)-1-(5-propyl-1,3,4-thiadiazol-2-yl)ethyl)-2-(4-methylpiperazin-1-yl)thiazole-5-carboxamide

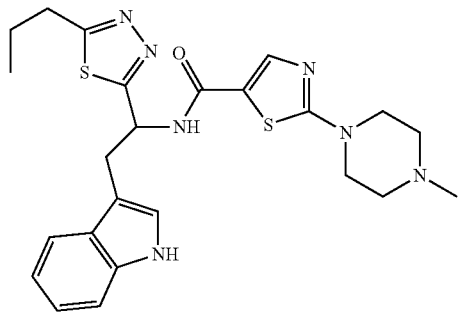 [SMILES: CCCc1nnc(C(Cc2c[nH]c3ccccc23)NC(=O)c2cnc(N3CCN(C)CC3)s2)s1]

See description for Example 5.

Example 10

N-(2-(1H-indol-3-yl)-1-(5-propyl-4H-1,2,4-triazol-3-yl)ethyl)-2-(4-methylpiperazin-1-yl)thiazole-5-carboxamide

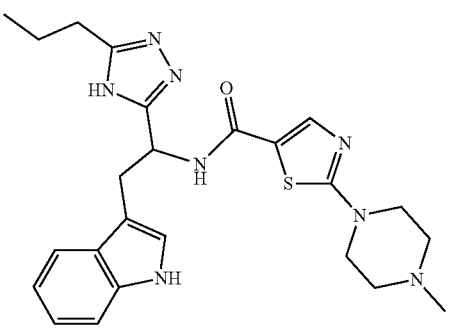 [SMILES: CCCc1nnc(C(Cc2c[nH]c3ccccc23)NC(=O)c2cnc(N3CCN(C)CC3)s2)[nH]1]

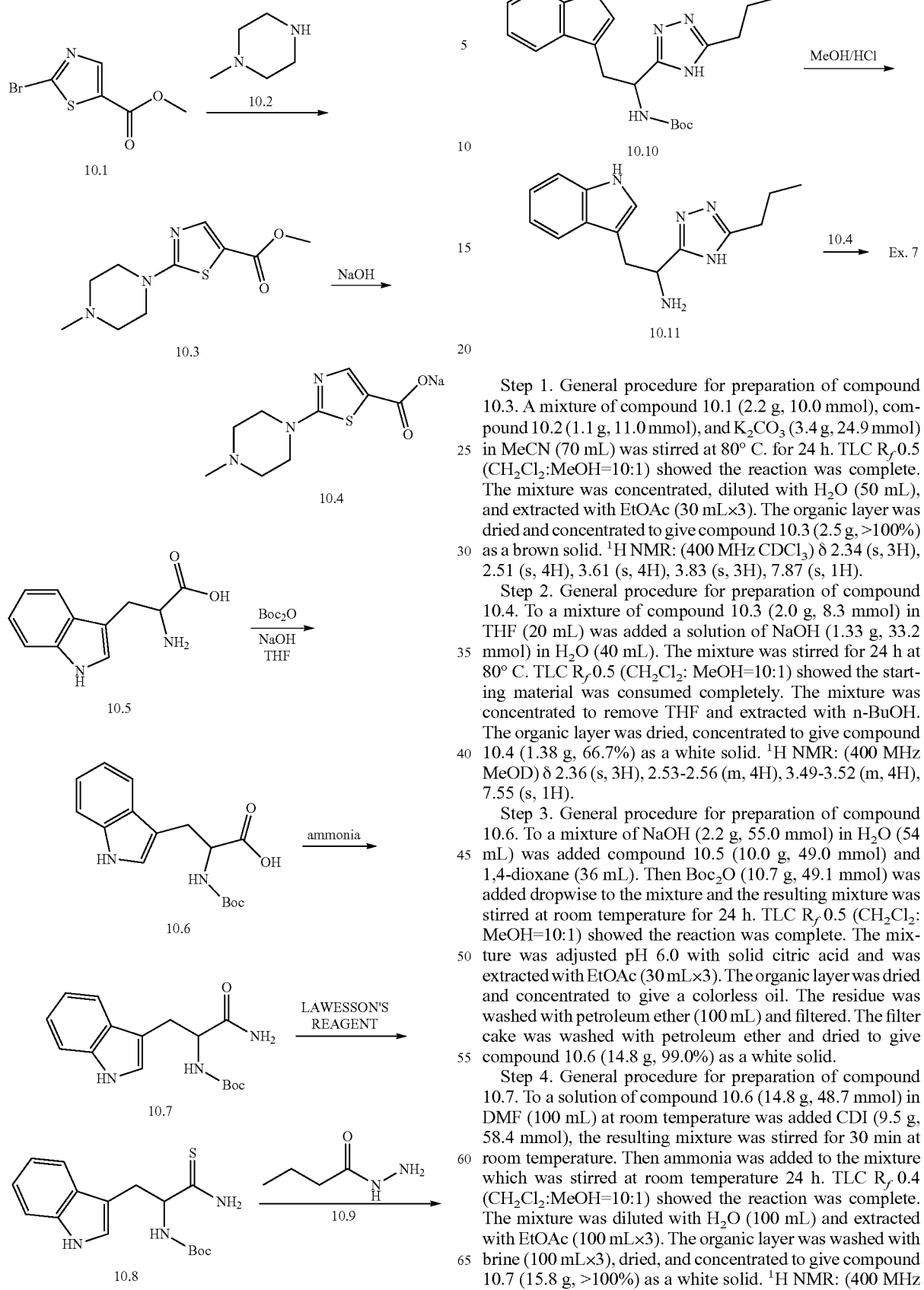

General Scheme:

Step 1. General procedure for preparation of compound 10.3. A mixture of compound 10.1 (2.2 g, 10.0 mmol), compound 10.2 (1.1 g, 11.0 mmol), and K$_2$CO$_3$ (3.4 g, 24.9 mmol) in MeCN (70 mL) was stirred at 80° C. for 24 h. TLC R$_f$ 0.5 (CH$_2$Cl$_2$:MeOH=10:1) showed the reaction was complete. The mixture was concentrated, diluted with H$_2$O (50 mL), and extracted with EtOAc (30 mL×3). The organic layer was dried and concentrated to give compound 10.3 (2.5 g, >100%) as a brown solid. $^1$H NMR: (400 MHz CDCl$_3$) δ 2.34 (s, 3H), 2.51 (s, 4H), 3.61 (s, 4H), 3.83 (s, 3H), 7.87 (s, 1H).

Step 2. General procedure for preparation of compound 10.4. To a mixture of compound 10.3 (2.0 g, 8.3 mmol) in THF (20 mL) was added a solution of NaOH (1.33 g, 33.2 mmol) in H$_2$O (40 mL). The mixture was stirred for 24 h at 80° C. TLC R$_f$ 0.5 (CH$_2$Cl$_2$: MeOH=10:1) showed the starting material was consumed completely. The mixture was concentrated to remove THF and extracted with n-BuOH. The organic layer was dried, concentrated to give compound 10.4 (1.38 g, 66.7%) as a white solid. $^1$H NMR: (400 MHz MeOD) δ 2.36 (s, 3H), 2.53-2.56 (m, 4H), 3.49-3.52 (m, 4H), 7.55 (s, 1H).

Step 3. General procedure for preparation of compound 10.6. To a mixture of NaOH (2.2 g, 55.0 mmol) in H$_2$O (54 mL) was added compound 10.5 (10.0 g, 49.0 mmol) and 1,4-dioxane (36 mL). Then Boc$_2$O (10.7 g, 49.1 mmol) was added dropwise to the mixture and the resulting mixture was stirred at room temperature for 24 h. TLC R$_f$ 0.5 (CH$_2$Cl$_2$: MeOH=10:1) showed the reaction was complete. The mixture was adjusted pH 6.0 with solid citric acid and was extracted with EtOAc (30 mL×3). The organic layer was dried and concentrated to give a colorless oil. The residue was washed with petroleum ether (100 mL) and filtered. The filter cake was washed with petroleum ether and dried to give compound 10.6 (14.8 g, 99.0%) as a white solid.

Step 4. General procedure for preparation of compound 10.7. To a solution of compound 10.6 (14.8 g, 48.7 mmol) in DMF (100 mL) at room temperature was added CDI (9.5 g, 58.4 mmol), the resulting mixture was stirred for 30 min at room temperature. Then ammonia was added to the mixture which was stirred at room temperature 24 h. TLC R$_f$ 0.4 (CH$_2$Cl$_2$:MeOH=10:1) showed the reaction was complete. The mixture was diluted with H$_2$O (100 mL) and extracted with EtOAc (100 mL×3). The organic layer was washed with brine (100 mL×3), dried, and concentrated to give compound 10.7 (15.8 g, >100%) as a white solid. $^1$H NMR: (400 MHz DMSO) δ 1.31 (s, 7H), 2.93-2.96 (m, 1H), 3.08-3.13 (m, 1H), 4.07-4.21 (m, 2H), 6.63-6.65 (d, J=8 Hz, 1H), 6.95-6.99 (t, J=8 Hz, 1H), 7.03-7.07 (t, J=8 Hz, 1H), 7.14 (s, 1H), 7.32-7.33 (d, J=4 Hz, 1H), 7.39 (s, 1H), 7.60-7.62 (d, J=8 Hz, 1H), 10.78 (s, 1H).

Step 5. General procedure for preparation of compound 10.8. A mixture of compound 10.7 (15.8 g, 52.1 mmol) in THF (160 mL) was treated with Lawesson's reagent (26.3 g, 25.2 mmol). The mixture was stirred for 5 h at 80° C. TLC $R_f$ 0.6 ($CH_2Cl_2$:MeOH=10:1) showed the reaction was complete. The mixture was concentrated to remove THF, and the residue was dissolved in $CH_2Cl_2$ (100 mL) and washed with $H_2O$ (100 mL*3). The organic layer was concentrated purified by silica gel column ($CH_2Cl_2$:MeOH=1:0-10:1) to give crude compound 10.8 (14.0 g, 84%) as a yellow solid which was used for next step directly.

Step 6. General procedure for preparation of compound 10.10. To a solution of compound 10.8 (1.0 g, 3.1 mmol) and compound 10.9 (0.32 g, 3.1 mmol) in n-BuOH (10 mL) was added $Cs_2CO_3$ (3.0 g, 9.4 mmol), and the resulting mixture was sealed and heated in the microwave at 85° C. for 3 h. TLC $R_f$ 0.6 ($CH_2Cl_2$:MeOH=10:1) showed the reaction was complete. The mixture was diluted with EtOAc (100 mL) and washed with $H_2O$ (60 mL×3). The combined organic layers were dried and concentrated. The residue was purified by silica gel column ($CH_2Cl_2$:MeOH=1:0-10:1) to give compound 10.10 (3.1 g, 24.4%, combined with other 10 batches) as an orange solid. $^1$H NMR: (400 MHz DMSO) δ 0.83-0.88 (m, 3H), 1.32 (s, 7H), 1.63-1.65 (d, J=8 Hz, 2H), 2.56 (s, 2H), 3.24-3.25 (d, J=4 Hz, 1H), 5.06-5.08 (d, J=8 Hz, 1H), 5.64-5.65 (d, J=4 Hz, 1H), 6.90-6.94 (t, J=16 Hz, 1H), 7.00-7.04 (d, J=16 Hz, 1H), 7.14-7.16 (d, J=8 Hz, 1H), 7.31-7.33 (d, J=8 Hz, 1H), 8.25 (s, 1H).

Step 7. General procedure for preparation of compound 10.11. A solution of compound 10.10 (2.0 g, 5.4 mmol) in MeOH/HCl (10 mL) was stirred for 2 h at room temperature. TLC $R_f$ 0.4 ($CH_2Cl_2$:MeOH=10:1) showed the reaction was complete. The mixture was adjusted pH 12 with solution of NaOH (2 M), and extracted with EtOAc (30 mL×5). The organic layer was dried and concentrated to give compound 10.11 (1.0 g, 68.5%) as an orange solid. $^1$H NMR: (400 MHz DMSO) δ 0.86-0.90 (d, J=8 Hz, 2H), 1.63-1.72 (m, 2H), 2.59-2.63 (t, J=8 Hz, 2H), 2.96-3.02 (m, 1H), 3.25-3.30 (m, 1H), 4.30-4.33 (m, 1H), 6.77 (s, 1H), 6.94-6.98 (t, J=8 Hz, 1H), 7.04-7.08 (d, J=8 Hz, 1H), 7.18-7.20 (m, 1H), 7.39-7.41 (d, J=8 Hz, 1H), 8.43 (s, 1H).

Step 8. General procedure for preparation of Example 10. To a mixture of compound 10.11 (0.5 g, 1.86 mmol) in solvent $CH_2Cl_2$ (20 mL) and THF (2 mL) was added compound 10.4 (0.69 g, 2.79 mmol). Then PyBOP (1.16 g, 2.23 mmol) and DIPEA (0.96 g, 7.44 mmol) were added to the mixture which was stirred for 24 h at room temperature under $N_2$ atmosphere. TLC $R_f$ 0.5 ($CH_2Cl_2$:MeOH=10:1) showed the reaction was complete. The mixture was diluted with $H_2O$ (20 mL) and extracted with $CH_2Cl_2$ (10 mL×3). The combined organic layers were dried over $Na_2SO_4$ and concentrated. The residue was purified by preparative HPLC (Shimadzu LC-8A prep-HPLC; Column: Luna(2) C18, 250×50 mm i.d. 10u; Mobile phase: A for $H_2O$ (0.09% TFA) and B for $CH_3CN$; Gradient: B %=5% to 30% in 23 min; Flow rate: 80 mL/min; Wavelength: 220 and 254 nm; 0.6 g per injection) to give Example 10 (249 mg, 28%) as white solid. $^1$H NMR: (400 MHz DMSO) δ 0.95-0.99 (t, J=8 Hz, 3H), 1.28 (s, 1H), 1.72-1.82 (m, 3H), 2.32 (s, 3H), 2.44 (s, 4H), 2.66-2.70 (t, J=8 Hz, 2H), 3.39-3.50 (m, 6H), 5.60-5.62 (d, J=8 Hz, 1H), 6.99-7.11 (m, 3H), 7.21-7.23 (d, J=8 Hz, 1H), 7.41-7.46 (d, J=8 Hz, 2H), 8.50 (s, 1H); MS: (M+1$^+$): 479.3; HPLC: 98.23%.

Example 11

N-(2-(1H-indol-3-yl)-1-(5-propyl-1,2,4-oxadiazol-3-yl)ethyl)-2-(4-methylpiperazin-1-yl)thiazole-5-carboxamide

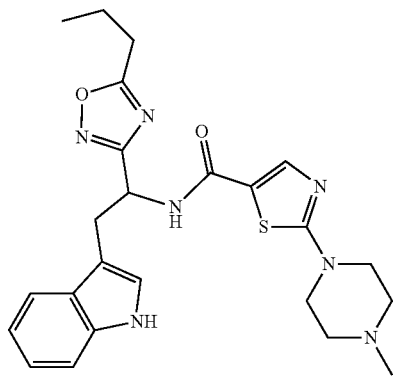 [SMILES: CCCc1nc(C(Cc2c[nH]c3ccccc23)NC(=O)c2cnc(N3CCN(C)CC3)s2)no1]

See description for Example 5.

Example 12

N-(2-(1H-indol-3-yl)-1-(5-propyl-1,3,4-oxadiazol-2-yl)ethyl)-2-(4-methylpiperazin-1-yl)thiazole-5-carboxamide

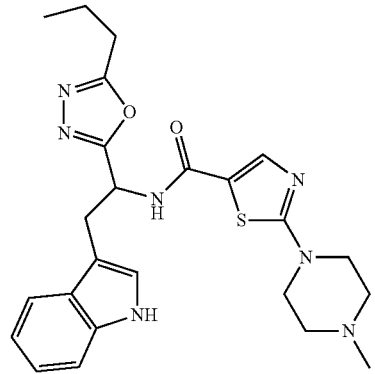 [SMILES: CCCc1nnc(C(Cc2c[nH]c3ccccc23)NC(=O)c2cnc(N3CCN(C)CC3)s2)o1]

See description for Example 5.

Example 26

In Vitro Cell-Free and Cell-Based Assays

Cell-Free Assay.
Recombinant α-synuclein (10 μM) are incubated at 37° C. for 16 h and then at 56° C. for 6 h with test compound. Control experiments are performed with inactive compounds that do not recognize α-synuclein, with β- and γ-synuclein and a mutant α-synuclein molecule. After incubation, the mixture is run on a SDS-PAGE gel, followed by immunoblot testing with α-synuclein antibodies. The study tests the ability of test compounds to inhibit the aggregation of α-synuclein into oligomers.

Cell-Based Assays.

(a) Aggregation. A neuronal cell line infected with lentivirus (LV) expressing α-synuclein (wild type) or empty vector (control) is exposed to test compounds at a range of concentrations, such as 0.01-10 µM, for 24 h. Cells are analyzed for α-synuclein aggregation by immunoblot and confocal microscopy. By immunoblot, compared to controls, neuronal cells infected LV-α-synuclein display high levels of expression of SYN monomer (14 kDa) as well as oligomers consistent with dimers, trimers, and tetramers in the soluble and insoluble fractions. After treatment with test compound, the reduction in the levels of aggregates in the various fractions is measured. Treatment with vehicle or with a control inactive compound has no effect on the levels of α-synuclein. In similar manner, by confocal microscopy, compared to LV-empty vector control, neuronal cells infected with LV-α-synuclein show high levels of α-synuclein accumulation (similar to what is observed in the brains of SYN Tg mice and patients with PD). After treatment with test compounds, the reduction in the level of aggregates in the neuronal cell bodies and neurites is measured.

(b) Neuronal Activity/Integrity. Toxic aggregates of α-synuclein disrupt the integrity of cell membranes. The disruptive effect of α-synuclein and the ability of test compounds to reverse the α-synuclein-mediated disruption of cell membranes are measured using calcein. Calcein is a fluorescent marker that is retained in healthy cells but is not retained in cells with diminished cellular integrity. To ascertain the effects on neuronal activity, cells are infected with LV-α-synuclein for 24 h, treated with test compound at a range of concentrations, for example 0.01-10 µM, for 24 h in serum free media, loaded with Fluo-4 or calcein, and analyzed by FLIPR assay to determine $Ca^{2+}$ and calcein levels. Compared to LV-empty vector control, neuronal cells infected with LV-α-synuclein showed 25-30% higher levels of $Ca^{2+}$. Test compounds are evaluated for the ability to restore concentrations of $Ca^{2+}$ to those in cells not infected with LV-α-synuclein. Treatment with vehicle or with a control inactive compound has no effect on $Ca^{2+}$ levels. Compared to LV-empty vector control, neuronal cells infected with LV-α-synuclein showed a 50% decrease in calcein retention in the cytoplasm. Test compounds are evaluated, in a concentration-dependent manner, for their ability to reverse the effect of α-synuclein on levels of calcein. Treatment with vehicle or with a control inactive compound is unable to re-establish calcein levels.

Data for compounds tested in the calcein assay of membrane integrity are presented in the following table:

| Ex. | Percent reversal of α-Syn mediated disruption of cell integrity (0.01 µM test compound) |
| --- | --- |
| 5 | 110 |
| 6 | 137 |
| 7 | 189 |
| 8 | 135 |
| 9 | 187 |
| 10 | 115 |

(c) Neuronal Survival. To examine the effects of test compounds on neuronal survival, an MTT cell viability assay is performed. Test compounds are evaluated for toxic effects at doses ranging, for example, from 0.01-10 µM.

Example 27

In Vivo Assay

In vivo efficacy of test compounds is assessed in α-synuclein transgenic (Tg) mice. Mice are analyzed behaviorally, neuropathologically, and biochemically for α-synuclein aggregation and neurodegeneration. Blood and CSF are analyzed for levels of α-synuclein and test compound by mass spectrometry and NMR. A Tg mouse model of PD is used that overexpresses wild-type human α-synuclein under the Thy1 promoter in a mixed C57B16/DBA background (Rockenstein E, Mallory M, Hashimoto M, Song D, Shults C W, Lang I, Masliah E (2002) Differential neuropathological alterations in transgenic mice expressing alpha-synuclein from the platelet-derived growth factor and Thy-1 promoters. J Neurosci Res., 68(5):568-78) (referred to as Line 61 tg mice). This Tg mouse develops progressive PD-like motor deficits and neuropathological indices (including alpha-synuclein aggregates and decreases in synaptic markers) starting at 3 months of age (Fleming S M, Salcedo J, Fernagut P O, Rockenstein E, Masliah E, Levine M S, Chesselet M F (2004) Early and progressive sensorimotor anomalies in mice overexpressing wild-type human alpha-synuclein. J Neurosci., 24(42):9434-40). Accordingly, treatments begin in animals at 3 months of age and motor behaviors (locomotor activity and round beam performance test, as well as neuropathological and biochemically measures for a-synuclein aggregation and neurodegeneration) are assessed after 3 months of treatment at 6 months of age.

Compound administration: Test compounds are dissolved in a vehicle solution and administered at a volume of 0.1 cc per 10 grams of body weight. Animals receive a Monday-Friday daily intraperitoneal injection of vehicle or 10 mg/kg of test compound for 90 days. Behavioral assessments are conducted starting on or about day 80 of treatment.

Locomotor Activity Apparatus and testing procedure: Locomotor activity data are collected over four consecutive days using a Kinder SmartFrame Cage Rack Station activity monitor system (Kinder Scientific, Poway, Calif.). The locomotor activity testing regimen consists of four sessions (15 min ea) on four consecutive days. On each test day, each individual animal is placed into the test chamber and then data collection begins immediately. Data are processed and imported into MS Excel for subsequent analysis and graphing using GraphPad Prism (GraphPad Software, Inc., La Jolla, Calif.). Dependent measures for spontaneous locomotor activity analyzed for each animal include investigatory rearings, total distance travelled, % of time spent in periphery, % of time spent in center, and thigmotaxis. Group means are derived for each measure and analyzed by a 2-way ANOVA with genotype and treatment group as between-subjects factors. In the event of main effects or interactions, post hoc comparisons are made using Bonferroni's multiple comparisons test. The criterion for statistical significance is $p<0.05$.

Round Beam Apparatus & testing procedure: Round beam data are collected using a custom built apparatus consisting of removable 2 Delrin® acetel plastic rods (3 and 1 cm diameter) on a smooth acrylic frame elevated 17.5 to 22.5 cm above a testing bench. Each animal is tested consecutively for three trials on each 1 meter beam A (3 cm) and D (1 cm) with a brief break between each trial. Using a manual counter, each obvious foot slip past the marked line is counted by the experimenter. In addition, forward distance travelled (assessed using marked 10 cm sections on side of beam and then assigned a score) and the latency to fall (60 sec max.) for each trial is recorded for each animal. The trial ends when animal falls off the beam, reaches the maximum allowed time (60 seconds), or traverses the full distance. Raw data are recorded by hand and then entered into MS Excel for subsequent analysis and graphing using GraphPad Prism (GraphPad Software, Inc., La Jolla, Calif.). The dependent measures for performance on each diameter beam include: # of foot slips, forward distance travelled, and latency to fall. These measures are determined for each animal and presented as the mean±the standard error of the mean (SEM). Group means are determined for each measure and analyzed by a 2-way ANOVA with genotype and treatment group as between-subjects factors. In the event of main effects or interactions, post hoc comparisons are made using Bonferonni's multiple comparisons test. The criterion for statistical significance is $p<0.05$.

Neuropathology: At the completion of behavioral assessments and treatment, tissue collection, processing, and imaging methods are conducted as described previously (Masliah E, Rockenstein E, Veinbergs I, Mallory M, Hashimoto M, Takeda A, Sagara, Sisk A, Mucke L (2000) Dopaminergic loss and inclusion body formation in alpha-synuclein mice: implications for neurodegenerative disorders. Science 287: 1265-1269). Briefly, brains and peripheral tissues are removed and divided sagitally. The right hemibrain is post-fixed in phosphate-buffered 4% PFA (pH 7.4) at 4° C. for 48 h for neuropathological analysis, while the left hemibrain is snap-frozen and stored at −70° C. for subsequent RNA and protein analysis. Drop fixed hemibrains are then serially sectioned into 40 μM thick coronal sections using a vibratome. Sections are free-floated and incubated overnight at 4° C. with primary antibodies. To confirm the specificity of primary antibodies, control experiments are performed in which sections are incubated overnight in the absence of primary antibody (deleted), preimmune serum, or primary antibody preadsorbed for 48 h with 20-fold excess of the corresponding peptide. Immunolabeling studies of alpha-synuclein are conducted using polyclonal rabbit anti-alpha-synuclein antibodies (1:1000; Millipore, Temecula, Calif.) with studies of oligomers conducted following proteinase K digestion. Immunolabeling studies of neurodegeneration-relevant markers utilize antibodies (Millipore, Temecula, Calif.) against NeuN (1:1000, ABN78), MAP2 (1:40, AB5622), synaptophysin (1:100, MAB5258) and GFAP (1:500, AB5804) antibodies. Imaging and analysis is performed on blindcoded sections from tg and non-tg mice, as described previously by Masliah and colleagues (Masliah et al., 2000).

Ex vivo Western blot protein analysis: Processing of the cytosolic (soluble) and membrane (insoluble) fractions of mouse brain homogenates is performed as previously described (Hashimoto M, Rockenstein E, Mante M, Mallory M, Masliah E (2001) beta-Synuclein inhibits alpha-synuclein aggregation: a possible role as an anti-parkinsonian factor. Neuron, 32(2):213-23) for SDS-PAGE analysis. Briefly, for each fraction, 20 μg is loaded per lane using 4-12% Bis-Tris gels (Invitrogen, Carlsbad, Calif.). Electrophoresis onto PDGF membranes (Millipore, Temecula, Calif.) is followed by: (1) blocking, (2) incubation with primary antibodies; (3) incubation with secondary antibodies; (4) ECL visualization (PerkinElmer, Wellseley, Mass.); (4) imaging and analysis using a VersaDoc gel imaging system (Bio-Rad, Hercules, Calif.) with graphing and statistical analyses performed using GraphPad Prism (GraphPad Software, Inc., La Jolla, Calif.).

The invention claimed is:

1. A compound of Formula I:

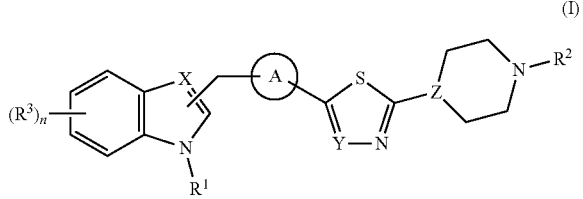

(I)

wherein
X, Y, and Z are each independently CH or N;
$R^1$ is H, $C_{1-6}$alkyl, or $C_{3-7}$cycloalkyl;
$R^2$ is H, $C_{1-6}$alkyl, or $C_{3-7}$cycloalkyl;
each $R^3$ is independently halogen, hydroxy, $C_{1-4}$alkoxy, cyano, amino, or —$CF_3$;
n is 0, 1, or 2; and
A moiety is:
(a) a 5-membered heteroaryl ring substituted with $C_{1-6}$alkyl; or

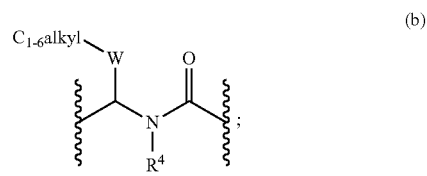

(b)

wherein W is a 5-membered heteroaryl ring, —C(O)NHNHC(O)—, —C(NH)NH—, or —C(O)NHNH—; and
$R^4$ is H or $C_{1-6}$alkyl;
or a pharmaceutically acceptable salt thereof.

2. The compound of claim 1, wherein X is CH.

3. The compound of claim 1, wherein Y is CH.

4. The compound of claim 1, wherein Y is N.

5. The compound of claim 1, wherein Z is CH.

6. The compound of claim 1, wherein Z is N.

7. The compound of claim 1, wherein $R^1$ is H or methyl.

8. The compound of claim 1, wherein $R^2$ is H or methyl.

9. The compound of claim 1, wherein n is 0 or 1.

10. The compound of claim 1, wherein A moiety is a 5-membered heteroaryl ring substituted with $C_{1-6}$alkyl.

11. The compound of claim 1, wherein A moiety is pyrrolyl, pyrazolyl, imidazolyl, furanyl, oxazolyl, oxadiazolyl, thienyl, thiazolyl, thiadiazolyl, triazolyl, or tetrazolyl, each substituted with $C_{1-6}$alkyl.

12. The compound of claim 1, wherein A moiety is

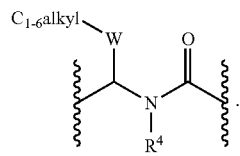

13. The compound of claim 1, wherein W is a 5-membered heteroaryl ring.

14. The compound of claim 1, wherein W is pyrrolyl, pyrazolyl, imidazolyl, furanyl, oxazolyl, oxadiazolyl, thienyl, thiazolyl, thiadiazolyl, triazolyl, or tetrazolyl.

15. The compound of claim 1, wherein W is —C(O)NHNHC(O)—, —C(NH)NH—, or —C(O)NHNH—.

16. The compound of claim 1, wherein $R^4$ is H, methyl, ethyl, propyl, or isopropyl.

17. The compound of claim 1, wherein A moiety is imidazolyl or triazolyl, each substituted with $C_{1-6}$alkyl.

18. The compound of claim 1, wherein A moiety is

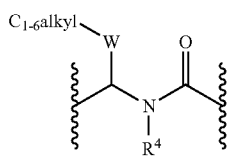

and W is —C(O)NHNHC(O)—, —C(NH)NH—, —C(O)NHNH—, tetrazolyl, thiazolyl, thiadiazolyl, triazolyl, or oxadiazolyl.

19. A compound selected from the group consisting of:

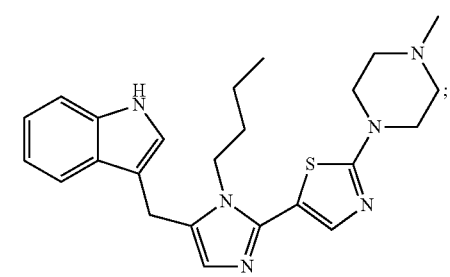

5-(5-((1H-indol-3-yl)methyl)-1-butyl-1H-imidazol-2-yl)-2-(4-methylpiperazin-1-yl)thiazole

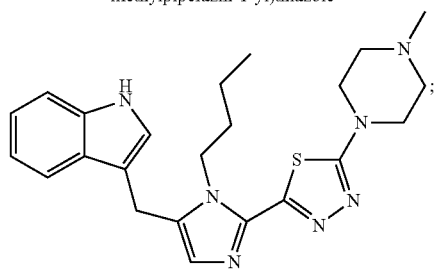

2-(5-((1H-indol-3-yl)methyl)-1-butyl-1H-imidazol-2-yl)-5-(4-methylpiperazin-1-yl)-1,3,4-thiadiazole

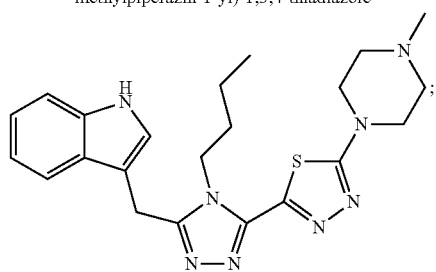

2-(5-((1H-indol-3-yl)methyl)-4-butyl-4H-1,2,4-triazol-3-yl)-5-(4-methylpiperazin-1-yl)-1,3,4-thiadiazole

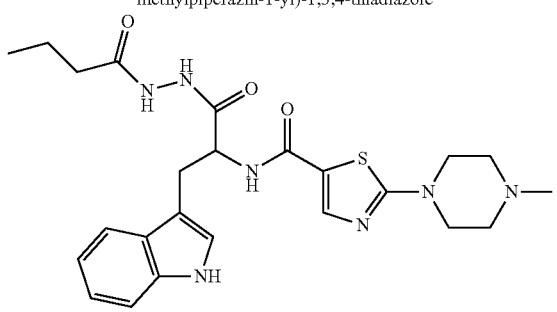

N-(1-(2-butyrylhydrazinyl)-3-(1H-indol-3-yl)-1-oxopropan-2-yl)-2-(4-methylpiperazin-1-yl)thiazole-5-carboxamide

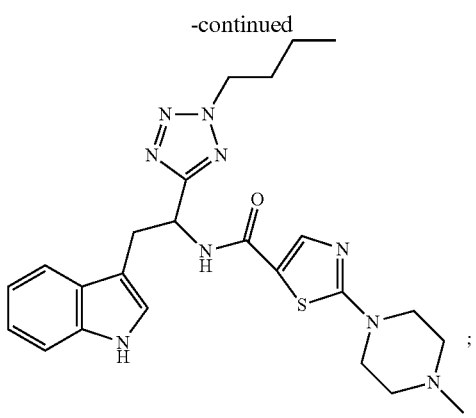

N-(1-(2-butyl-2H-tetrazol-5-yl)-2-(1H-indol-3-yl)ethyl)-2-(4-methylpiperazin-1-yl)thiazole-5-carboxamide

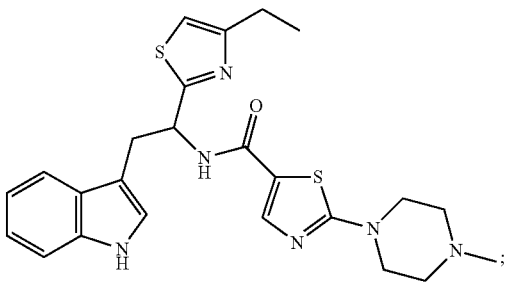

N-(1-(4-ethylthiazol-2-yl)-2-(1H-indol-3-yl)ethyl)-2-(4-methylpiperazin-1-yl)thiazole-5-carboxamide

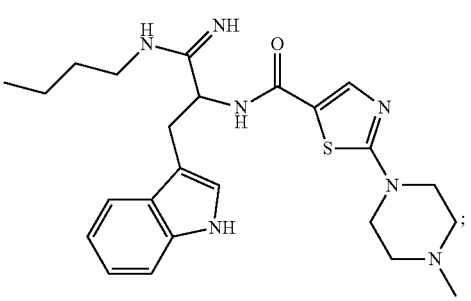

N-(1-(butylamino)-1-imino-3-(1H-indol-3-yl)propan-2-yl)-2-(4-methylpiperazin-1-yl)thiazole-5-carboxamide

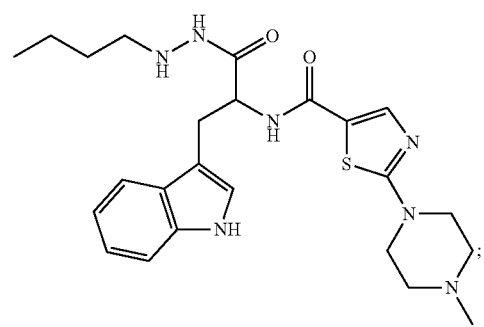

N-(1-(2-butylhydrazinyl)-3-(1H-indol-3-yl)-1-oxopropan-2-yl)-2-(4-methylpiperazin-1-yl)thiazole-5-carboxamide -continued

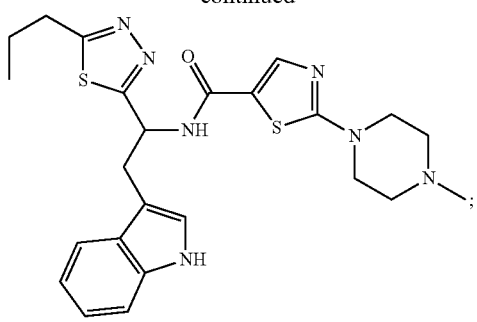

N-(2-(1H-indol-3-yl)-1-(5-propyl-1,3,4-thiadiazol-2-yl)ethyl)-2-(4-methylpiperazin-1-yl)thiazole-5-carboxamide

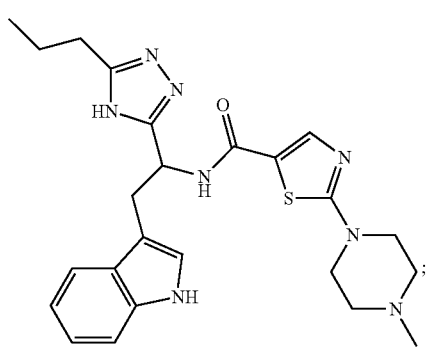

N-(2-(1H-indol-3-yl)-1-(5-propyl-4H-1,2,4-triazol-3-yl)ethyl)-2-(4-methylpiperazin-1-yl)thiazole-5-carboxamide

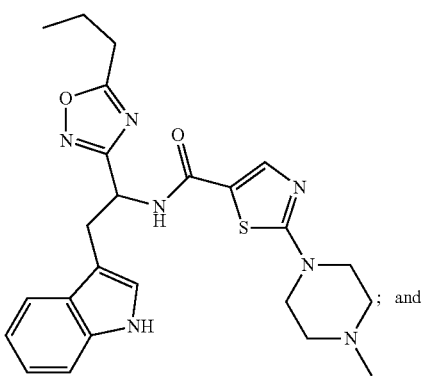

N-(2-(1H-indol-3-yl)-1-(5-propyl-1,2,4-oxadiazol-3-yl)ethyl)-2-(4-methylpiperazin-1-yl)thiazole-5-carboxamide -continued

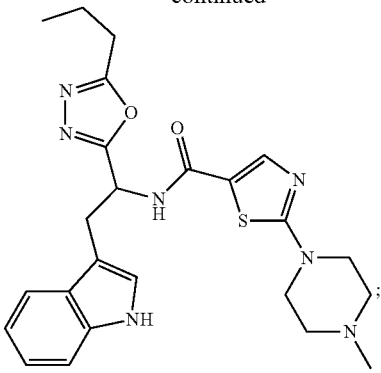

N-(2-(1H-indol-3-yl)-1-(5-propyl-1,3,4-oxadiazol-2-yl)ethyl)-2-(4-methylpiperazin-1-yl)thiazole-5-carboxamide and pharmaceutically acceptable salts thereof.

20. A pharmaceutical composition comprising (a) at least one compound of Formula I:

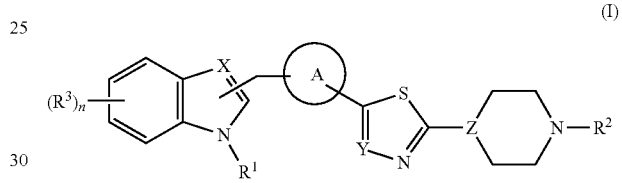

(I)

wherein
X, Y, and Z are each independently CH or N;
$R^1$ is H, $C_{1-6}$alkyl, or $C_{3-7}$cycloalkyl;
$R^2$ is H, $C_{1-6}$alkyl, or $C_{3-7}$cycloalkyl;
each $R^3$ is independently halogen, hydroxy, $C_{1-4}$alkoxy, cyano, amino, or —$CF_3$;
n is 0, 1, or 2; and
A moiety is:
(a) a 5-membered heteroaryl ring substituted with $C_{1-6}$alkyl; or

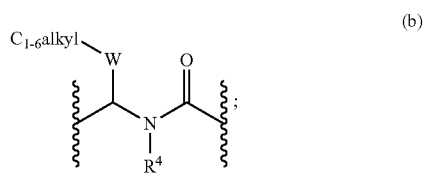

(b)

wherein W is a 5-membered heteroaryl ring, —C(O)NHNHC(O)—, —C(NH)NH—, or —C(O)NHNH—; and
$R^4$ is H or $C_{1-6}$alkyl;
or a pharmaceutically acceptable salt thereof, and
(b) a pharmaceutically acceptable excipient.

* * * * *